(12) United States Patent
Deshaies et al.

(10) Patent No.: US 9,493,833 B1
(45) Date of Patent: Nov. 15, 2016

(54) METHODS FOR PREVENTING INDUCED SYNTHESIS OF PROTEASOMES IN HUMAN CELLS

(75) Inventors: Raymond J. Deshaies, Claremont, CA (US); Senthil Radhakrishnan, Pasadena, CA (US); Candy S. Lee, Diamond Bar, CA (US); Jefferson Y. Chan, Irvine, CA (US)

(73) Assignees: THE REGENTS OF THE UNIVERSITY OF CALIFORNIA, Oakland, CA (US); CALIFORNIA INSTITUTE OF TECHNOLOGY, Pasadena, CA (US)

( * ) Notice: Subject to any disclaimer, the term of this patent is extended or adjusted under 35 U.S.C. 154(b) by 888 days.

(21) Appl. No.: 12/941,959

(22) Filed: Nov. 8, 2010

Related U.S. Application Data

(60) Provisional application No. 61/258,984, filed on Nov. 6, 2009, provisional application No. 61/315,195, filed on Mar. 18, 2010.

(51) Int. Cl.
| | | |
|---|---|---|
| *C12Q 1/68* | (2006.01) | |
| *G01N 33/574* | (2006.01) | |
| *A61K 48/00* | (2006.01) | |
| *A61K 38/00* | (2006.01) | |

(52) U.S. Cl.
CPC ............. *C12Q 1/6883* (2013.01); *A61K 38/00* (2013.01); *A61K 48/00* (2013.01)

(58) Field of Classification Search
None
See application file for complete search history.

(56) References Cited

U.S. PATENT DOCUMENTS

| | | | | |
|---|---|---|---|---|
| 2006/0019256 A1* | 1/2006 | Clarke et al. | ...................... | 435/6 |
| 2006/0281122 A1* | 12/2006 | Bryant et al. | ...................... | 435/6 |
| 2011/0009353 A1* | 1/2011 | Chen-Kiang et al. | .......... | 514/34 |

OTHER PUBLICATIONS

Andrews, et al., "*Erythroid transcription factor NF-E2 is a haematopoietic-specific basic-leucine zipper protein*", Nature, vol. 362, Apr. 22, 1993, pp. 722-728.
Altavilla, et al., "*Amplification and overexpression of the PSMB5 gene contributes to bortezomib resistance in retreatment of patients with multiple myeloma*", Journal of Clinical Oncology, vol. 27, No. 15S, May 20, 2009 Supplement (Abstract Only).
Arlt, et al., "*Increased proteasome subunit protein expression and proteasome activity in colon cancer relate to an enhanced activation of nuclear factor E2-related factor 2 (Nrf2)*", Oncogene, vol. 28, Sep. 7, 2009, pp. 3983-3996.
Bazzaro, et al., "*Ubiquitin-Proteasome System Stress Sensitizes Ovarian Cancer to Proteasome Inhibitor-Induced Apoptosis*", Cancer Research, vol. 66, No. 7, Apr. 1, 2006, pp. 3754-3763.
Berg, et al., "*Negative Regulation of Inducible Nitric-oxide Synthase Expression Mediated through Transforming Growth Factor-β-dependent Modulation of Transcription Factor TCF11*", The Journal of Biological Chemistry, vol. 282, No. 51, Dec. 21, 2007, pp. 36837-36844.
Biswas, et al., "*Role of Nrf1 in antioxidant response element-mediated gene expression and beyond*", Toxicology and Applied Pharmacology, vol. 244, 2010 (available online 2009), pp. 16-20.
Caterina, et al. "*Cloning and functional characterization of LCR-F1: a bZIP transcription factor that activates erythroid-specific, human globin gene expression*", Nucleic Acids Research, vol. 22, No. 12, 1994, pp. 2383-2391.
Chan, et al., "*Targeted disruption of the ubiquitous CNC-bZIP transcription factor, Nrf-1, results in anemia and embryonic lethality in mice*" The EMBO Journal, vol. 17, No. 6, 1998, pp. 1779-1787.
Chan, et al. "*NRF2, a member of the NFE2 family of transcription factors, is not essential for murine erythropoiesis, growth, and development*", PNAS USA, vol. 93, Nov. 1996, pp. 13943-13948.
Chen, et al., "*Increased Proteasome Activity, Ubiquitin-Conjugating Enzymes, and eEF1A Translation Factor Detected in Breast Cancer Tissue*", Cancer Research, vol. 65, No. 13, Jul. 1, 2005, pp. 5599-5606.
Ciechanover, "*Proteolysis: from the lysosome to ubiquitin and the proteasome*", Nature Reviews Molecular Cell Biology, vol. 6, Jan. 2005, pp. 79-86.
Demo, et al, "*Antitumor Activity of PR-171, a Novel Irreversible Inhibitor of the Proteasome*", Cancer Research, vol. 67, No. 13, Jul. 1, 2007, pp. 6383-6391.
Dohmen, et al., "*Biting the hand that feeds: Rpn4-dependent feedback regulation of proteasome function*", Biochemica et Biophysica Acta (BBA), vol. 1773, 2007, pp. 1599-1604.
Fan, et al., "*Application of Bioluminescence and Cell-Based Assays in High-Throughput Screening Studies*", Cell Notes, Issue 20, 2008, pp. 30-32.
Farmer, et al., "*The bZIP transcription factor LCR-F1 is essential for mesoderm formation in mouse development*", Genes & Development, vol. 11, 1997, pp. 786-798 (also includes cover page).
Finley, "*Recognition and Processing of Ubiquitin-Protein Conjugates by the Proteasome*", Annual Review of Biochemistry, vol. 78, 2009, pp. 477-513 (also includes 3 sheets with Table of Contents).
Glickman, et al., "*A Subcomplex of the Proteasome Regulatory Particle Required for Ubiquitin-Conjugate Degradation and Related to the COP9-Signalosome and eIF3*", Cell, vol. 94, Sep. 4, 1998, pp. 615-623.
Groll, et al., "*Structure of 20S proteasome from yeast at 2.4 Å resolution*", Nature, vol. 386, Apr. 3, 1997, pp. 463-471.
Johnsen, et al. "*Interaction of the CNC-bZIP factor TCF11/LCR-F1/Nrf1 with MafG: binding-site selection and regulation of transcription*", Nucleic Acids Research, vol. 26, No. 2, 1998, pp. 512-520.
Kensler, et al., "*Cell Survival Responses to Environmental Stresses Via the Keap1-Nrf2-ARE Pathway*", Annual Review of Pharmacology and Toxicology, vol. 47, 2007, pp. 89-116 (also includes 2 sheets with Table of Contents).

(Continued)

*Primary Examiner* — Catherine S Hibbert
*Assistant Examiner* — Channing S Mahatan
(74) *Attorney, Agent, or Firm* — Lewis Roca Rothgerber Christie LLP

(57) ABSTRACT

Methods and compositions for inhibiting Nrf1 activity are provided for enhancing apoptosis in mammalian cells. Apoptosis is enhanced in mammalian cells by co-inhibiting Nrf1 activity and proteasome activity. Methods for identifying Nrf1 inhibitors are provided using an assay for screening Nrf1 inhibitors that enhance proteasome inhibition by preventing induced proteasome expression.

11 Claims, 21 Drawing Sheets

(56) References Cited

OTHER PUBLICATIONS

Kisselev, et al., "Monitoring Activity and Inhibition of 26S Proteasomes with Fluorogenic Peptide Substrates", Methods in Enzymology, vol. 398, 2005, pp. 364-378.

Kobayashi, et al., "Molecular Cloning and Functional Characterization of a New Cap'n' Collar Family Transcription Factor Nrf3", The Journal of Biological Chemistry, vol. 274, No. 10, Issue of Mar. 5, 1999, pp. 6443-6452.

Kraft, et al., "Preincubation with the Proteasome Inhibitor MG-132 Enhances Proteasome Activity via the Nrf2 Transcription Factor in Aging Human Skin Fibroblasts", Annals New York Academy of Sciences, vol. 1067, 2006 pp. 420-424.

Kumatori, et al., "Abnormally high expression of proteasomes in human leukemic cells", PNAS USA, vol. 87, Sep. 1990, pp. 7071-7075.

Kusmierczyk, et al., "Some Assembly Required: Dedicated Chaperones in Eukaryotic Proteasome Biogenesis", Biol. Chem, vol. 389, No. 9, Sep. 2008, pp. 1143-1151 (15 sheets).

Kwak, et al., "Antioxidants Enhance Mammalian Proteasome Expression through the Keap1-Nrf2 Signaling Pathway", Molecular and Cellular Biology, vol. 23, No. 23, Dec. 2003, pp. 8786-8794.

Kwak, et al., "Induction of 26S proteasome subunit PSMB5 by the bifunctional inducer 3-methylcholanthrene through the Nrf2-ARE, but not the AhR/Arnt-XRE, pathway", Biochemical and Biophysical Research Communications, vol. 345, 2006, pp. 1350-1357.

Lamb, et al., "The Connectivity Map: Using Gene-Expression Signatures to Connect Small Molecules, Genes, and Disease", Science, vol. 313, Sep. 29, 2006, pp. 1929-1935 (also includes cover page).

Lundgren, et al., "Identification and Characterization of a Drosophila Proteasome Regulatory Network", Molecular and Cellular Biology, vol. 25, No. 11, Jun. 2005, pp. 4662-4675.

Mannhaupt, et al., "Rpn4p acts as a transcription factor by binding to PACE, a nonamer box found upstream of 26S proteasomal and other genes in yeast", Federatrion of European Biochemical Societies Letters, vol. 450, 1999, pp. 27-34.

Meiners, et al., "Inhibition of Proteasome Activity Induces Concerted Expression of Proteasome Genes and de Novo Formation of Mammalian Proteasomes" The Journal of Biological Chemistry, vol. 278, No. 24, Issue of Jun. 13, 2003, pp. 21517-21525.

Mitisiades, et al., "Molecular sequelae of proteasome inhibition in human multiple myeloma cells", PNAS, vol. 99, No. 22, Oct. 29, 2002, pp. 14374-14379.

Moi, et al. "Isolation of NF-E2-related factor 2 (Nrf2), a NF-E2-like basic leucine zipper transcriptional activator that binds to the tandem NF-E2/AP1 repeat of the β-globin locus control region", PNAS USA, vol. 91, Oct. 1994,pp. 9926-9930.

Murata, et al., "Molecular mechanisms of proteasome assembly", Nature Reviews Molecular Cell Biology, vol. 10, Feb. 2009, pp. 104-115.

Myhrstad, et al. "TCF11/Nrf1 overexpression increases the intracellular glutathione level and can transactivate the γ-glutamylcysteine synthetase (GCS) heavy subunit promoter", Biochimica et Biophysica Acta (BBA), vol. 1517, 2001, pp. 212-219.

Nakajima, et al. "FR901228, a Potent Antitumor Antibiotic, is a Novel Histone Deacetylase Inhibitor", Experimental Cell Research, vol. 241, Article No. EX984027, 1998, pp. 126-133.

Oerlemans, et al., "Molecular basis of bortezomib resistance: proteasome subunit $^2$5 (PSMB5) gene mutation and overexpression of PSMB5 protein", Blood, vol. 112, No. 6 Sep. 15, 2008, pp. 2489-2499 (also includes cover page).

Orolowski, et al., "Proteasome Inhibitors in Cancer Therapy: Lessons from the First Decade", Clinical Cancer Research, vol. 14, No. 6, Mar. 15, 2008, pp. 1649-1657.

Oyake, et al., "Bach Proteins Belong to a Novel Family of BTB-Basic Leucine Zipper Transcription Factors That Interact with MafK and Regulate Transcription through the NF-E2 Site", Molecular and Cellular Biology, vol. 16, No. 11, Nov. 1996, pp. 6083-6095.

Papandreou, et al., "Phase I Trial of the Proteasome Inhibitor Bortezomib in Patients With Advanced Solid Tumors With Observations in Androgen-Independent Prostate Cancer", Journal of Clinical Oncology, vol. 22, No. 11, Jun. 1, 2004, pp. 2108-2121.

Park, et al., "Hexameric assembly of the proteasomal ATPases is templated through their C termini", Nature, vol. 459, Jun. 11, 2009, pp. 866-871.

Pickart, et al., "Proteasomes and Their Kin: Proteases in the Machine Age", Nature Reviews, Molecular Cell Biology, vol. 5, Mar. 2004, pp. 177-187.

Pilarsky, et al., "Identification and Validation of Commonly Overexpressed Genes in Solid Pilarsky, Tumors by Comparison of Microarray Data", Neoplasia, vol. X, No. Y, 2004 (7 sheets).

Prince, et al., "Panobinostat (LBH589): a novel pan-deacetylase inhibitor with activity in T cell lymphoma", Hematology Meeting Reports, vol. 3, No. 1, 2009, pp. 33-38.

Radhakrishnan, et al., "Transcription Factor Nrf1 Mediates the Proteasome Recovery Pathway after Proteasome Inhibition in Mammalian Cells", Molecular Cell, vol. 38, Apr. 9, 2010, pp. 17-28.

Revill, et al., "Ecallantide; Plasma Kallikrein Inhibitor Treatment of Hereditary Angioedema", Drugs of the Future, vol. 32, No. 7, 2007, pp. 590-594 (20 sheets).

Roelofs, et al., "Chaperone-mediated pathway of proteasome regulatory particle assembly", Nature, vol. 459, Jun. 11, 2009, pp. 861-865.

Sankaranarayanan, et al., "Nrf3 Negatively Regulates Antioxidant-response Element-mediated Expression and Antioxidant Induction of NAD(P)H:Quinone Oxidoreductase1 Gene", The Journal of Biological Chemistry, vol. 279, No. 49, Issue of Dec. 3, 2004, pp. 50810-50817.

Schwartz, et al, "Pharmacology, Pharmacokinetics, and Practical Applications of Bortezomib", Oncology, vol. 18, No. 14, Dec. 2004, pp. 14-21.

Smith, "Keeping tabs on fluorescent tags", Nature Methods, vol. 4, No. 9, Sep. 2007, pp. 755-761 (8 sheets).

Soucy, et al., "An inhibitor of NEDD8-activating enzyme as a new approach to treat cancer", Nature, vol. 458, Apr. 9, 2009, pp. 732-737.

Steffen, et al., "Proteasomal Degradation is Transcriptionally Controlled by TCF11 via an ERAD-Dependent Feedback Loop", Molecular Cell, vol. 40, Oct. 8, 2010, pp. 147-158.

Torres, et al., "Effects of Aneuploidy on Cellular Physiology and Cell Division in Haploid Yeast", Science, vol. 317, Aug. 17, 2007, pp. 916-924 (also includes cover page).

Unno, et al., "The Structure of the Mammalian 20S Proteasome at 2.75 ç Resolution", Structure, vol. 10, May 2002, pp. 609-618.

Venugopal, et al., "Nrf1 and Nrf2 positively and c-Fos and Fra1 negatively regulate the human antioxidant response element-mediated expression of NAD(P)H:quinone oxidoreductase$_1$ gene", PNAS USA, vol. 93, Dec. 1996, pp. 14960-14965.

Wang, et al., "Rpn4 is a Physiological Substrate of the Ubr2 Ubiquitin Ligase", The Journal of Biological Chemistry, vol. 279, No. 53, Issue of Dec. 31, 2004, pp. 55218-55223.

Wang, et al., "Nrf1 is Targeted to the Endoplasmic Reticulum Membrane by an N-terminal Transmembrane Domain; Inhibition of Nuclear Translocation and Transacting Function", The Journal of Biological Chemistry, vol. 281, No. 28, Jul. 14, 2006, pp. 19676-19687.

Wang, et al., "Identification of polymorphic antioxidant response elements in the human genome", Human Molecular Genetics, vol. 16, No. 10, 2007, pp. 1188-1200.

Xie, et al., "RPN4 is a ligand, substrate, and transcriptional regulator of the 26S proteasome: A negative feedback circuit", PNAS, vol. 98, No. 6, Mar. 13, 2001, pp. 3056-3061.

Zhang, et al., "Negative regulation of the Nrf1 transcription factor by its N-terminal domain is independent of Keap1 : Nrf1, but not Nrf2, is targeted to the endoplasmic reticulum", Biochemical Journal, vol. 399, 2006, pp. 373-385.

\* cited by examiner

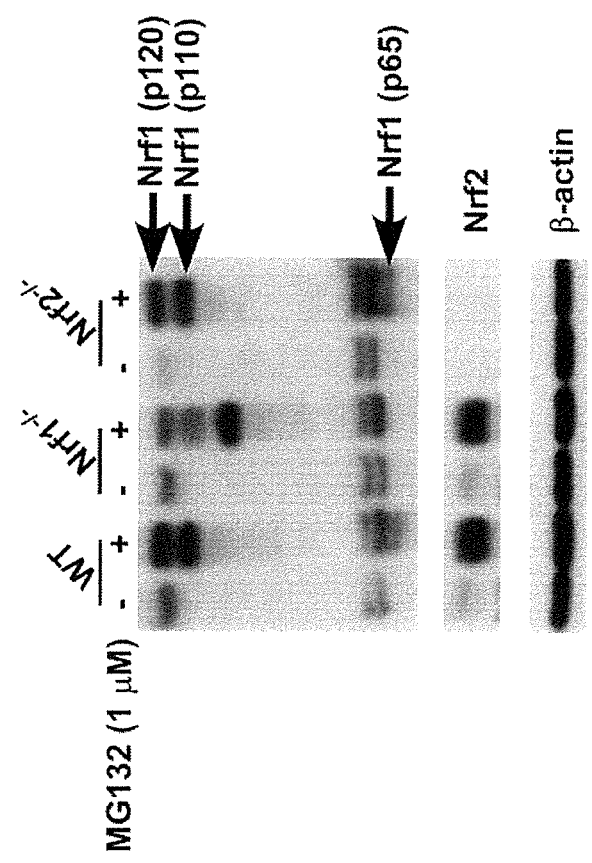

US 9,493,833 B1

METHODS FOR PREVENTING INDUCED SYNTHESIS OF PROTEASOMES IN HUMAN CELLS

CROSS-REFERENCE TO RELATED APPLICATION(S)

The present application claims priority to U.S. Provisional Application Ser. No. 61/258,984 filed Nov. 6, 2009 and U.S. Provisional Application Ser. No. 61/315,195 filed Mar. 18, 2010. The entire contents of the above-referenced applications are incorporated herein by reference.

STATEMENT REGARDING FEDERALLY SPONSORED RESEARCH OR DEVELOPMENT

The U.S. Government has certain rights in this invention pursuant to Grant No. W81XWH-07-1-0641 awarded by the ARO (Army Research Office).

INCORPORATION BY REFERENCE

The material in the text file entitled "64744SEQLISTING", prepared Nov. 8, 2010, being 9 kilobytes in size, and being filed concurrently with this application, is herein incorporated by reference in its entirety.

BACKGROUND

Proteasome inhibition has emerged as a viable mode of anti-cancer therapy (Orlowski and Kuhn, 2008, *Clin. Cancer Res.* 14, 1649-1657). Proteasome inhibitors induce apoptosis by preventing degradation of pro-apoptotic proteins, thereby facilitating activation of programmed cell death. With such pro-cancer effects, proteasome inhibitors, such as bortezomib, have found use in cancer therapy.

Inhibition of the proteasome induces new proteasome synthesis promoted by transcription factors. This transcriptional feedback mechanism is conserved in mammals and ensures that proteasome activity is matched to demand. Proteasome inhibition followed by proteasome gene upregulation is referred to as the proteasome "bounce-back" response.

As reported (Mitsiades, N., et al. 2002, *Proc Natl Acad Sci*, 99, 14374-14379), inhibition of the proteasome leads to upregulation of the proteasome (PSM) genes. As shown in FIGS. 1A-1C, human prostate cancer (LNCaP) and colon cancer (HT29) cell lines that were treated with different proteasome inhibitors (MG132, YU101, and bortezomib) induced transcription of several PSM genes that encode members of both the 20S (PSMA7, PSMB4, and PSMB7) and 19S (PSMC1, PSMC4, PSMD1, and PSMD12) complexes.

While some proteasome inhibitors dissociate from the proteasome allowing proteasome activity to resume (e.g. bortezomib), other proteasome inhibitors (e.g. YU101, carfilzomib) bind the proteasome irreversibly, such that proteasome recovery is solely dependent on new synthesis of proteasome genes. Furthermore, both bortezomib (an FDA-approved drug for the treatment of multiple myeloma) and carfilzomib (an experimental therapeutic) are rapidly cleared from the patients' blood within the first hour of their administration (Papandreou et al., 2004, *J. Clin. Oncol.*, 22, 2108-2121; Schwartz and Davidson, 2004, *Oncology*, (Williston Park), 19, (14, Suppl. 11), 14-21). Therefore, once the drug is cleared, proteasome activity recovers through a combination of the drug dissociating from the active site and new proteasome synthesis.

The extent and duration of proteasome inhibition that is achieved with bortezomib has been shown to be sufficient to kill many multiple myeloma tumor cells, but that does not ensure that bortezomib is sufficient for other cancers. In fact, bortezomib has shown limited efficacy in certain cancers, and resistance to bortezomib has also been observed (Orlowski and Kuhn, 2008). Accordingly, there is a need for improved cancer therapies through enhanced proteasome inhibition and prevention of induced proteasome synthesis.

SUMMARY

In one aspect of the present invention, a method of inducing apoptosis or expression of proteasome genes in mammalian cells is provided, that includes contacting the mammalian cells with a proteasome inhibitor; and contacting the mammalian cells with an inhibitor of nuclear factor erythroid-derived 2-related factor-1 (NFE2L1) gene product activity. For example, the NFE2L1 gene product is Nrf1 or Tcf11. In one embodiment, the inhibitor of the NFE2L1 gene product activity is RNAi targeted to the NFE2L1 gene. In a second embodiment, the inhibitor of the NFE2L1 gene is a histone deacetylase (HDAC) inhibitor. Examples of an HDAC inhibitor include TSA (trichostatin A), SAHA (suberoylanilide hydroxamic acid), romidepsin and panobinostat.

In a second aspect of the present invention, a method of identifying a compound that inhibits transcription mediated through an anti-oxidant response element (ARE) sequence in cells is provided, that includes transfecting a first population of cells with a reporter construct containing at least one anti-oxidant response element (ARE) sequence, a promoter, and a nucleic acid sequence corresponding to a reporter protein; contacting the first population of cells with a proteasome inhibitor; dividing the first population of cells into a non-test group and a test group; contacting a compound or a compound from a library of compounds with the test group; and measuring expression of the reporter protein in the non-test group and the test group, wherein a decrease in expression of the reporter protein in the test group, compared to the non-test group, indicates that the compound or the compound from the library of compounds inhibits expression of the reporter protein through the ARE sequence.

In an embodiment of the present invention, a method of identifying a compound that inhibits transcription mediated by an NFE2L1 gene product in cells is provided that includes transfecting a first population of the cells with a reporter construct containing at least one anti-oxidant response element (ARE) sequence, a promoter, and a nucleic acid sequence corresponding to a reporter protein; co-transfecting a second population of the cells with the reporter construct and an NFE2L1 gene product construct that overexpresses a tagged NFE2L1 gene product; contacting the first and second populations of cells with a proteasome inhibitor; dividing the first population of cells into a first non-test group and a first test group; dividing the second population of cells into a second non-test group and a second test group; contacting a compound or a compound from a library of compounds with the first test group and the second test group; and measuring expression of the reporter protein in the first and second populations of cells, wherein an increase in expression of the reporter protein in the second non-test group, compared to the first non-test group in combination with a decrease in expression of the first test group and the second test group compared to both the first non-test group and the second non-test group, indicates that the compound or the compound from the library of compounds inhibits the activity of the NFE2L1 gene product.

In a second embodiment of the present invention, a method of identifying a compound that inhibits NFE2L1 gene product activity in mammalian cells is provided that includes contacting the mammalian cells with a proteasome inhibitor; contacting the mammalian cells with a test compound; and measuring NFE2L1 gene product expression and/or gene synthesis.

In a third embodiment of the present invention, a host cell is provided, that includes a reporter construct containing at least one anti-oxidant response element (ARE) sequence, a promoter, and a nucleic acid sequence corresponding to a reporter protein; and an overexpressed NFE2L1 gene product.

BRIEF DESCRIPTION OF THE DRAWINGS

These and/or other aspects of the invention will become apparent and more readily appreciated from the following description of the embodiments, taken in conjunction with the accompanying drawings, wherein:

FIGS. 2A-2C show data from wildtype (WT), Nrf1–/– and Nrf2–/– cells; 2A shows a Western blot of Nrf1 and Nrf2 proteins in these cells; 2B-2C are graphs of the relative mRNA levels of proteasome genes in these cells in the presence of MG132;

DETAILED DESCRIPTION

Aspects of the present invention relate to methods and compounds for preventing the induced synthesis of proteasome genes and enhancing the apoptotic effects of proteasome inhibition by co-inhibition of a NFE2L1 (nuclear factor erythroid-derived 2-related factor 1) gene product. Aspects of the present invention also relate to methods for identifying compounds that inhibit NFE2L1.

As used herein, an NFE2L1 gene product refers to any gene product expressed from the NFE2L1 gene locus. In the art, the NFE2L1 gene locus is also referred to as NRF1, LCR-F1, NFE2L1 and TCF11 gene locus (Caterina et al., (1994), *Nucleic Acids Res.*, 22, 2382-2391; Chan et al., 1998, *EMBO J*, 17, 1779-1787). The Nrf1 protein and the TCF11 protein are splice variants of the NFE2L1 locus. Accordingly, the NRF1 gene locus is synonymous with the NFE2L1 gene locus, and Nrf1 activity is synonymous with NFE2L1 gene product activity.

Figure 2B:
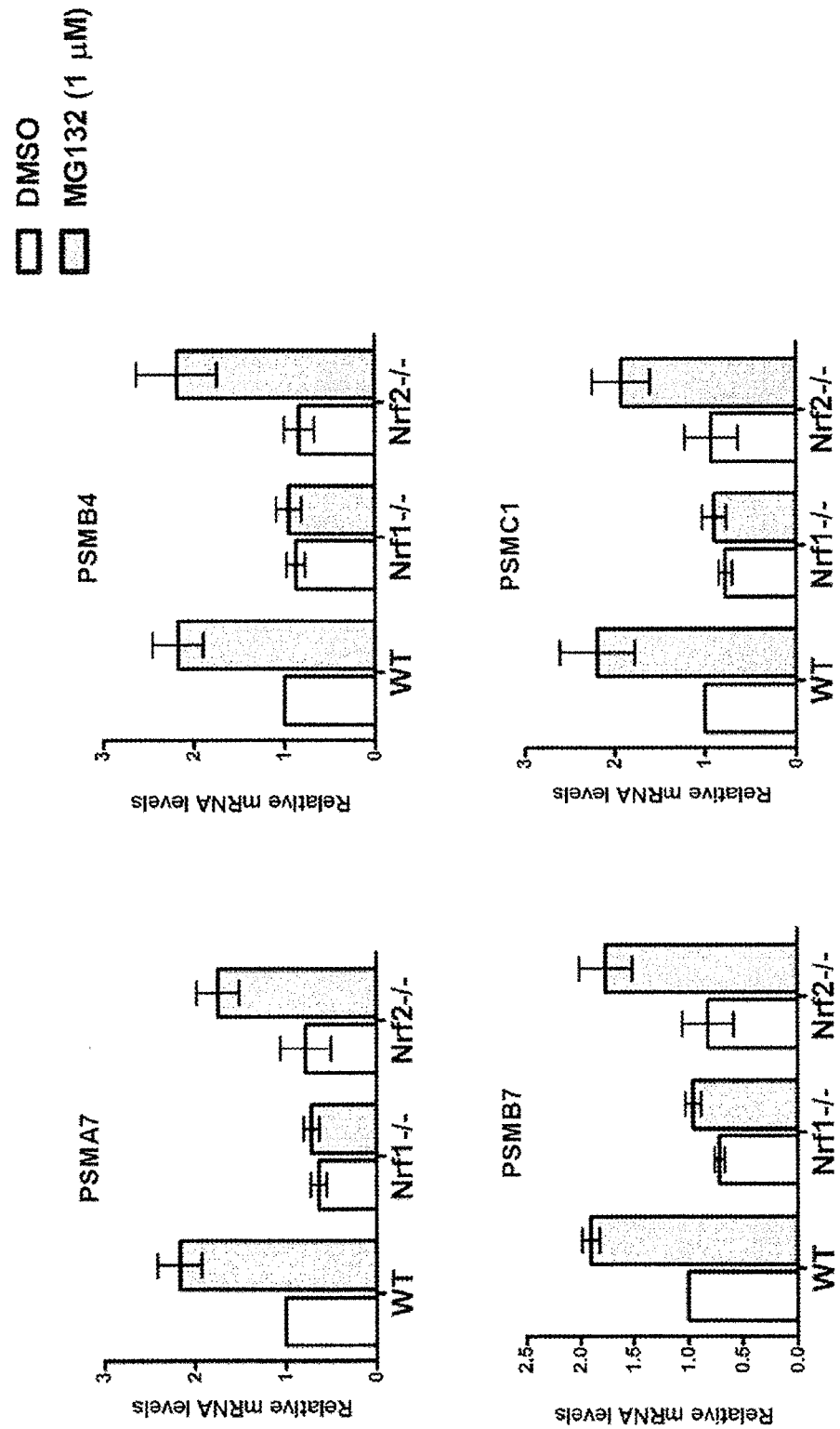
Figure 2C:
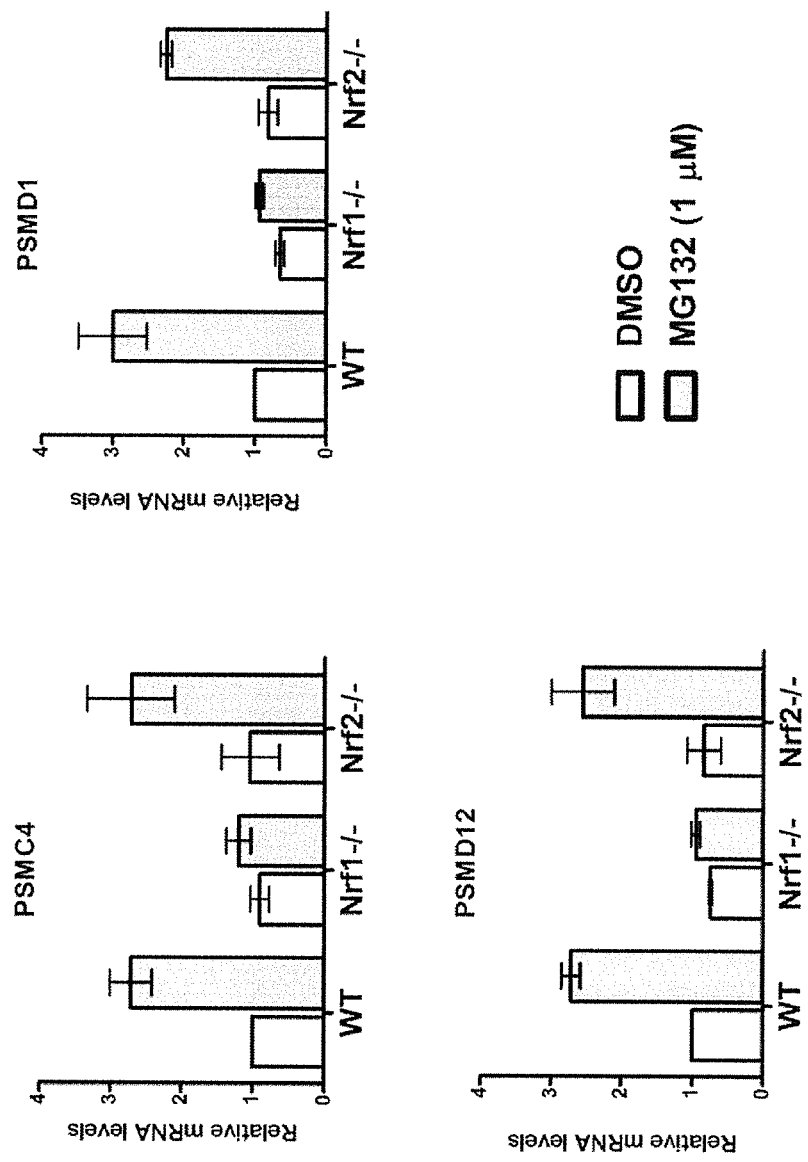

A first aspect of the invention relates to a method for co-inhibiting NFE2L1 gene product activity and proteasome activity in a cell. This co-inhibition of the NFE2L1 gene product and the proteasome relates to the finding that Nrf1 regulates synthesis of PSM genes, and that inhibition of Nrf1 further enhances the effects of a proteasome inhibitor. Specifically, it is shown that Nrf1 mouse embryonic fibroblasts (MEFs) that have the (Nrf1) gene locus knocked out (Chan et al., 1998)(FIG. 2A) are severely deficient in their ability to upregulate PSM genes in response to MG132 treatment (FIGS. 2B-2C). That is, upon inhibition of the proteasome in cells derived from Nrf1–/– mice (Nrf1–/– MEFs), the mRNA levels of proteasome genes remained essentially unchanged. Furthermore, overexpression of tagged-Nrf1 (FIG. 3A) induced PSM mRNA levels in untreated Nrf1–/– cells by approximately 1.5-2.0 fold compared to vector control (FIG. 3B), showing that the PSM gene regulation is specific to the NFR1 gene locus. The inability of Nrf1–/– cells to upregulate proteasome gene expression indicates an essential role for the NFR1 gene locus, and NFR1 gene products, in the proteasome bounce-back response, and indicates that co-inhibition of Nrf1 activity enhances proteasome inhibition.

As described in detail herein, a method is provided for inducing apoptosis in mammalian cells that includes inhibiting the Nrf1 gene locus or the activity of any Nrf1 gene product in combination with inhibiting proteasome activity. Inhibiting an Nrf1 gene product is carried out using any suitable method of inhibiting transcription from the Nrf1 gene locus, inhibiting translation of any Nrf1 transcript, or inhibiting the function of the Nrf1 protein.

Figure 4A:
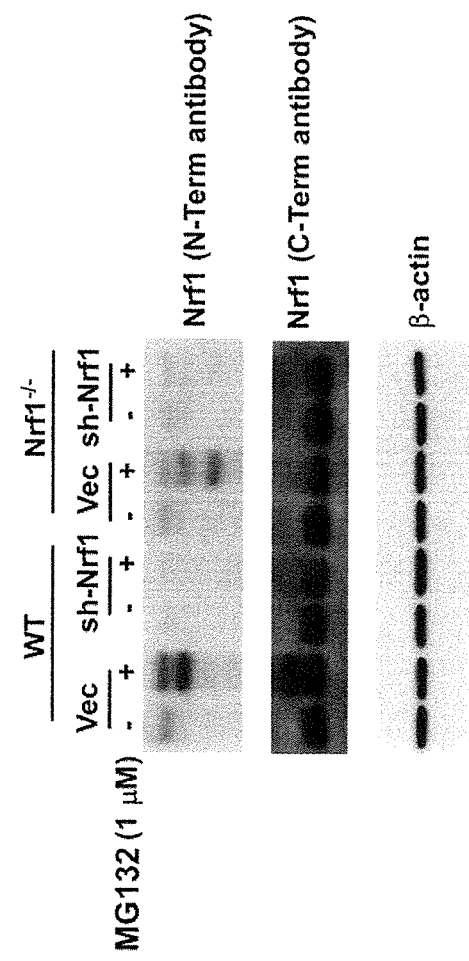
FIGS. 4A-4B show data of WT and Nrf1–/– cells expressing shNrf1 RNAi in the presence and absence of MG132; 4A shows a Western blot of Nrf1 protein; 4B are graphs of the relative mRNA levels of proteasome genes.
Figure 4B:
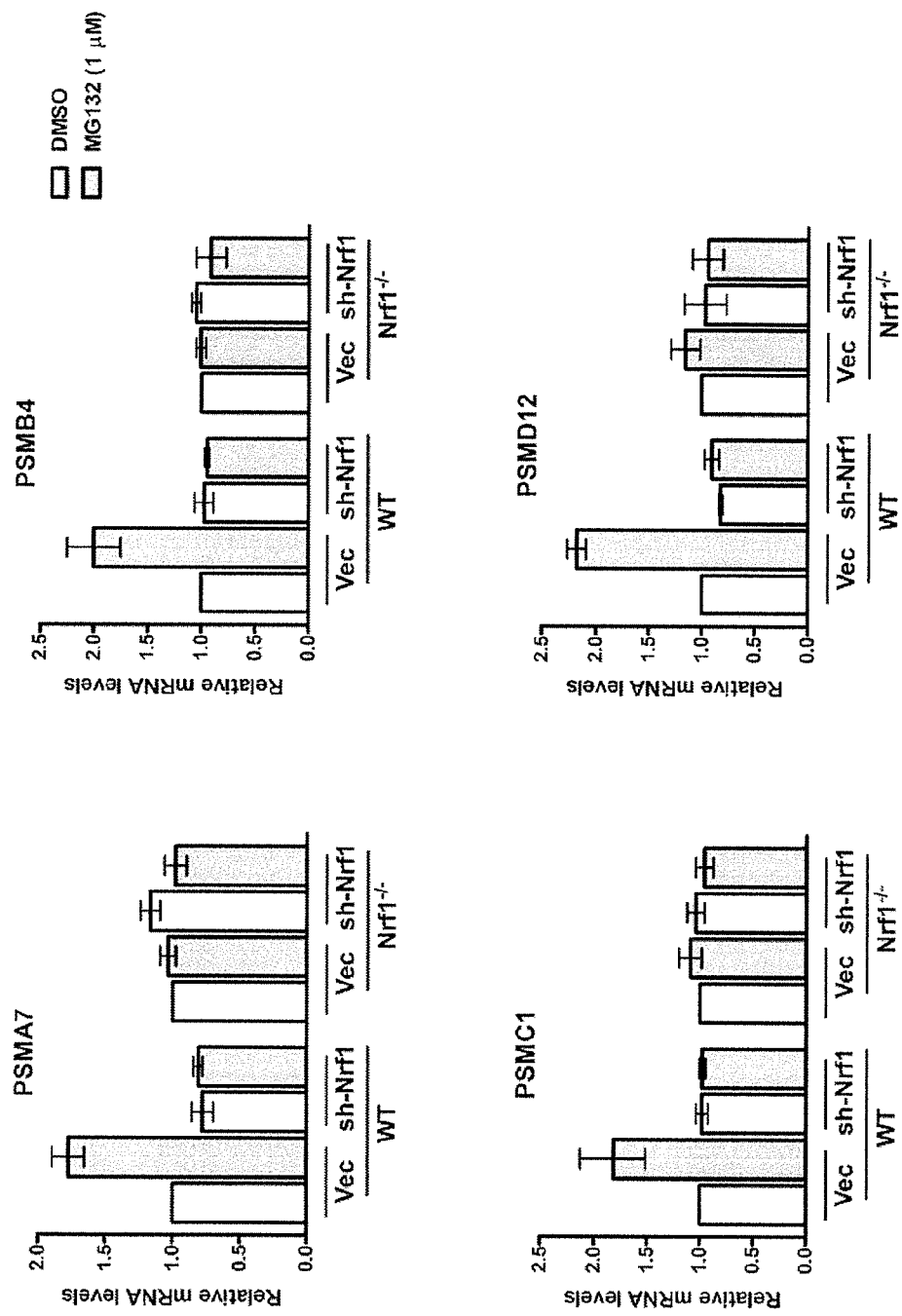

For example, in one embodiment of the present invention, inhibition of the Nrf1 transcript is carried out using RNAi which specifically binds to mRNA transcribed from the Nrf1 gene locus and induces its degradation. RNAi includes siRNA, shRNA and miRNA. Methods for designing RNAi targeted to specific genes and sequences are known in the art (Oligoengine, Halo-Bio RNAi Therapeutics, Inc., Seattle, Wash.). An example of RNAi inhibition of Nrf1 activity is shown in FIGS. 4A-4B. RNAi experiments were carried out with a retrovirus that expressed an shRNA that targets the 5' end of the Nrf1 mRNA corresponding to a 19 base pair sequence (SEQ ID NO: 1) of the NFE2L1 coding region. Knock-down of Nrf1 in wild type (WT) MEFs (FIG. 4A) mimicked the Nrf1$^{-/-}$ phenotype, in that MG132 did not induce accumulation of proteasome mRNAs in Nrf1-depleted cells (FIG. 4B). (See Example 4, and Materials and Methods)

Figure 5A:
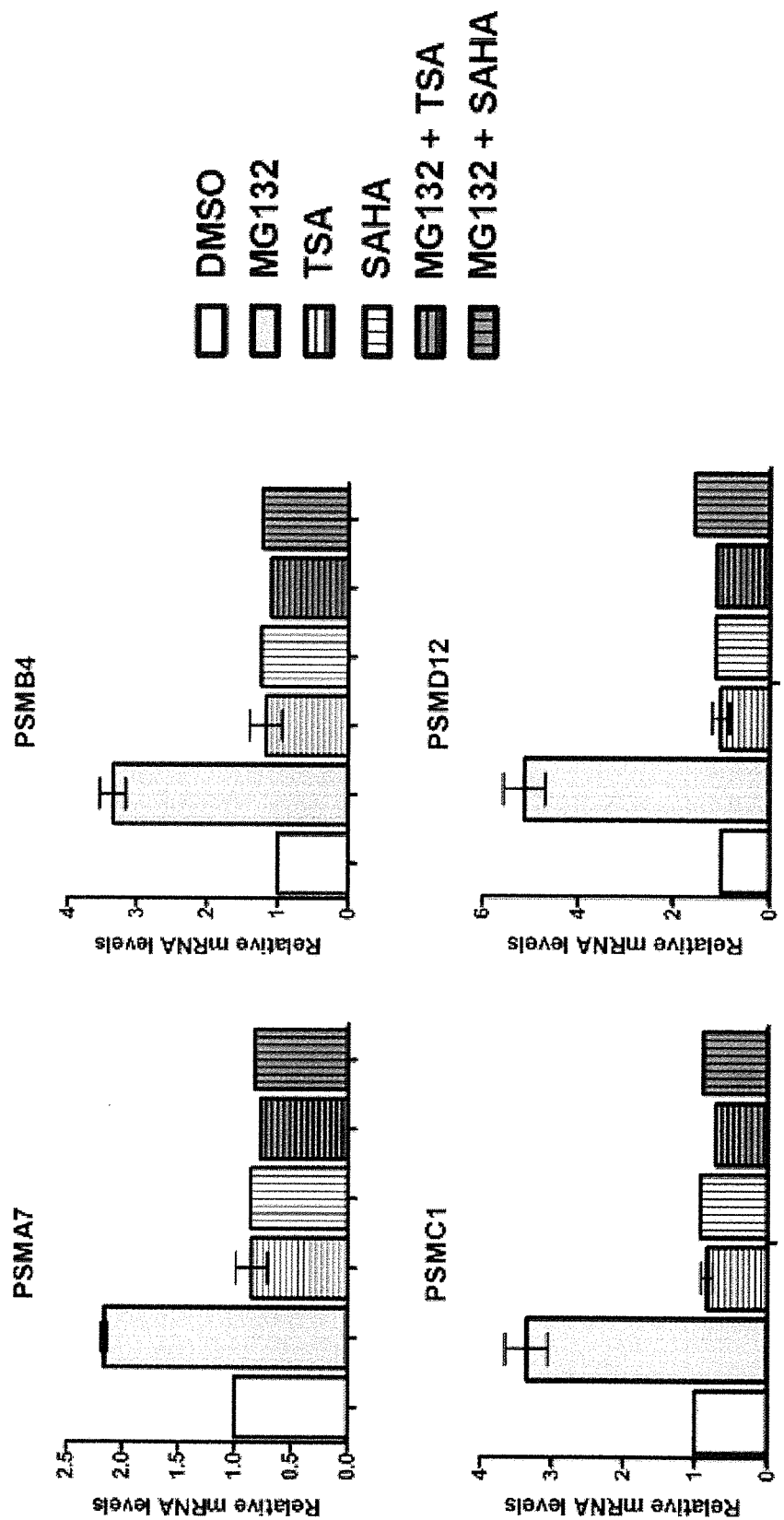
FIG. 5A-5B show data from inhibition of MG132 with TSA or SAHA in LNCaP and MDA-MB-231 cells; 5A is a graph of the relative mRNA levels of proteasome genes in LNCaP cells; 5B is a graph of cell viability in MDA-MB-231 cells.
Figure 5B:
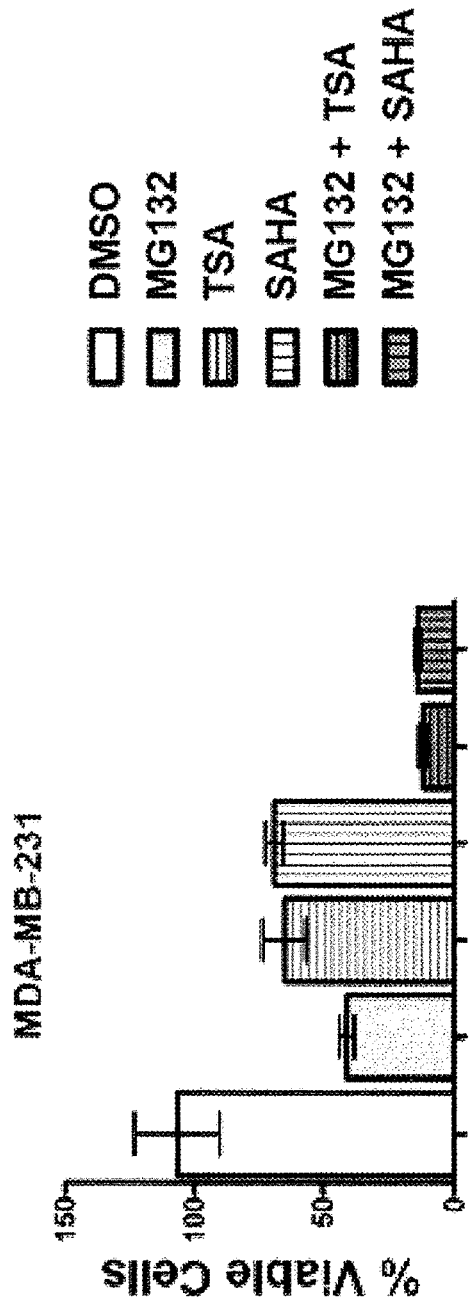

In a second aspect of the present invention, a method of identifying compounds that inhibit Nrf1 activity is provided and includes the steps detailed in the following reporter assay. Using a reporter assay of the present invention, the HDAC (histone deacetylase) inhibitors, TSA (trichostatin A) and SAHA (suberoylanilide hydroxamic acid), showed little effect on steady-state PSM gene expression, but reproducibly inhibited the MG132-mediated upregulation of representative PSM genes in LNCaP prostate cancer cells (FIG. 5A). Furthermore, MDA-MB-231 breast carcinoma cells showed enhanced apoptosis (decreased viability) when MG132 was combined with either TSA or SAHA (FIG. 5B). Accordingly, in one embodiment of the present invention, prevention of induced proteasome synthesis and induced apoptosis in mammalian cells is provided, by administering (contacting) a proteasome inhibitor in combination with an HDAC inhibitor. Other similar HDAC inhibitors include romidepsin and panobinostat. Romidepsin (1-R901228) functions similarly to TSA (Nakajima et al, *Experimental Cell Research* 241, 126-33). Panobinostat (LBH-589) is also a pan-HDAC inhibitor (Prince and Bishton, 2009, *Hematology Reports*, 3, 33-38; Revill et al., 2007, *Drugs of the Future*, 32, 315). For example, a method is provided for administering, TSA, SAHA, panobinostat or romidepsin in combination with a proteasome inhibitor.

As described in detail herein, (see Examples 5-6 and Materials and Methods), the reporter assay using an 8×ARE (anti-oxidant response element)-luciferase reporter construct and an Nrf1 construct is provided and utilized in mammalian cells to screen for inhibitors of an Nrf1 gene product in the presence of a proteasome inhibitor. This reporter assay using an ARE-reporter construct is based on a mechanistic link between Nrf1 activity and PSM gene expression in the context of the proteasome bounce-back response, as described herein. That is, as known, Nrf1 and the related transcription factors Nrf2 and Nrf3 bind to AREs (anti-oxidant response elements), a cis-acting enhancer sequence found in the promoter regions of their target genes, thereby regulating their transcription (Biswas and Chan, 2009, *Toxicol. Appl. Pharmacol.*, 244, 16-20; Johnsen et al., 1998, *Nucleic Acids Res.*, 26, 512-52-; Sankaranarayanan and Jaiswal, 2004, *J. Biol. Chem.*, 279, 50810-50817; Venugopal and Jaiswal, 1996, *Proc. Nat. Acad. Sci.*, 93, 14960-14965). To this end, a construct with an approximate 3 kb promoter region from murine PSMB6 was prepared and fused to a firefly luciferase reporter.

Figure 6:
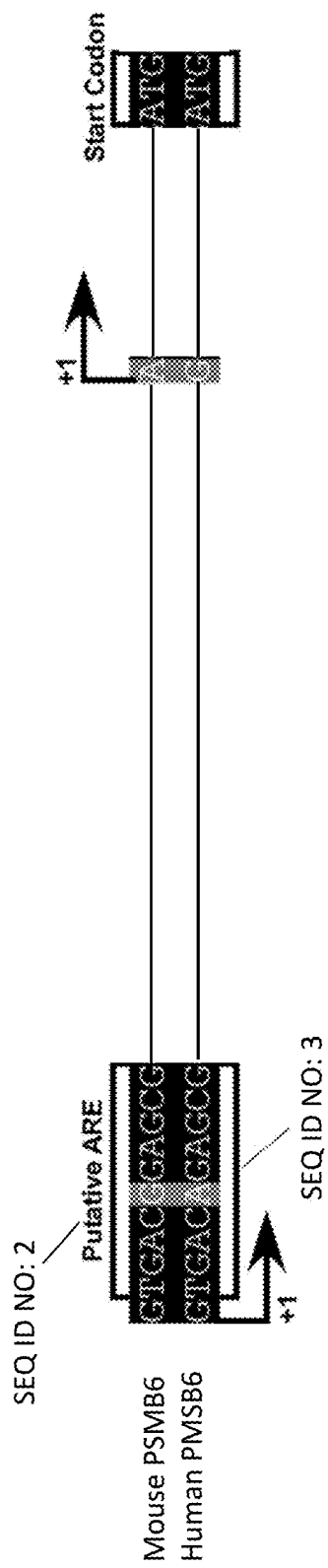
FIG. 6 is a graph of luciferase activity of the PSMB6-ARE-reporter construct in WT and Nrf1–/– MEFs in the presence of MG132.
Figure 7:
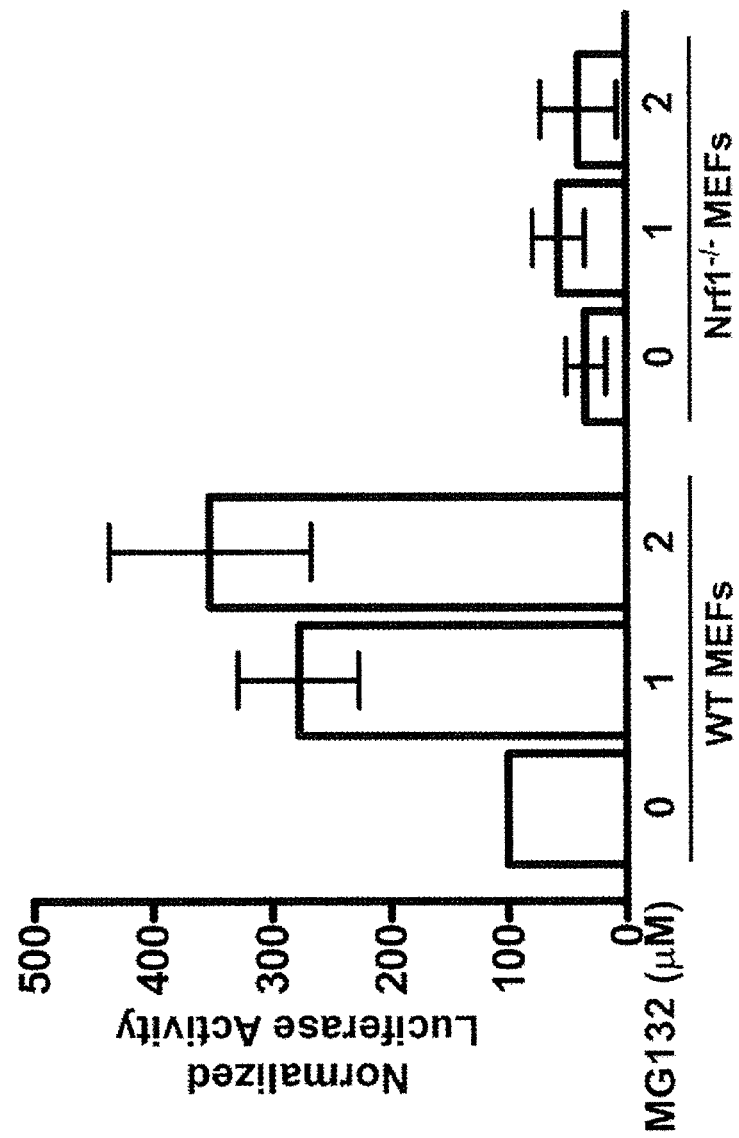
FIG. 7 shows a schematic of the 3×PSMA4-ARE and the 3×PSMA4-mutARE luciferase constructs.
Figure 8:
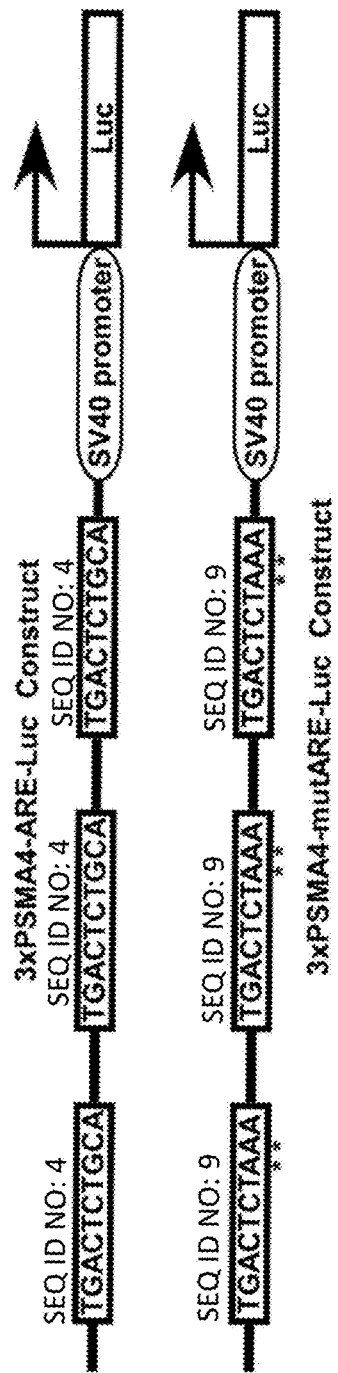
FIG. 8 is a graph of luciferase activity from the 3×PSMA4-ARE and the 3×PSMA4-mutARE luciferase constructs in LNCaP cells transfected with Flag-Nrf1 and in the presence of MG132.
Figure 9:
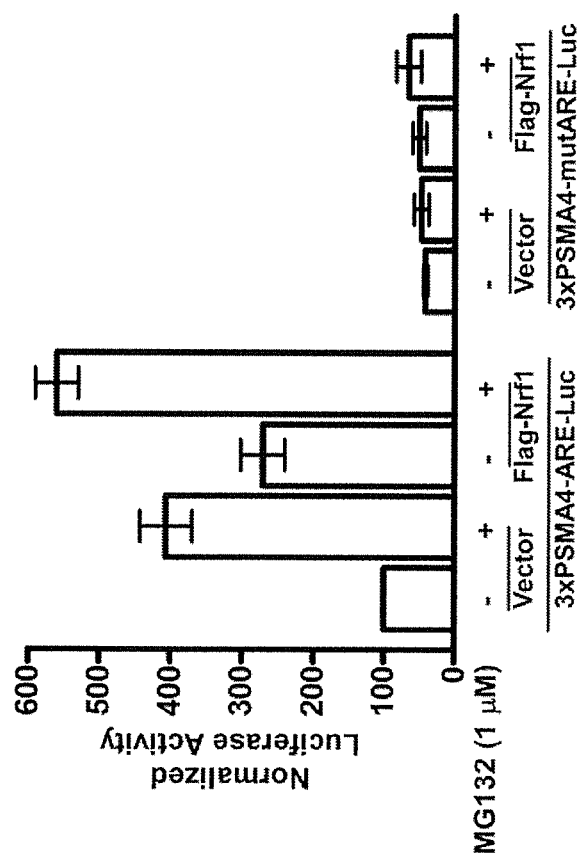
FIG. 9 shows alignment of human and mouse PSMB6 genes upstream of the start codons with boxes around the putative ARE and the start codon.

Using a position weight matrix that has been derived from functional AREs (Wang et al., 2007, *Human. Mol. Genet.* 16, 1188-1200), putative PSMB6 AREs (TGACAGAGCG) (SEQ ID NO: 2) and TGACGGAGCG (SEQ ID NO: 3) were computationally predicted that are close to the transcription start site of both the human and mouse PSMB6 genes (FIG. 6). Luciferase assays performed with the murine PSMB6 promoter-reporter construct, showed a dose dependent increase in luciferase activity after MG132 treatment of WT, but not Nrf1$^{-/-}$ MEFs (FIG. 7). To confirm the importance of AREs in this context, a synthetic promoter construct was generated in which three copies of a putative PSMA4 ARE (SEQ ID NO: 4) from the first intron of the human PSMA4 gene are inserted upstream of a minimal SV40 promoter driving the expression of a firefly luciferase reporter (FIG. 8). When LNCaP cells transfected with this construct were treated with MG132, an increase in luciferase activity was observed when compared to DMSO-treated control (FIG. 9).

Furthermore, it was found that overexpression of Flag-Nrf1 activated this synthetic promoter construct, and the luciferase activation was further enhanced when these cells were treated with MG132. In contrast, neither MG132 nor overexpressed Flag-Nrf1 induced the synthetic promoter construct when the AREs were mutated (FIG. 9). Accordingly, proteasome inhibition leads to Nrf1-dependent activation of PSM gene promoters specifically through AREs.

Figure 10:
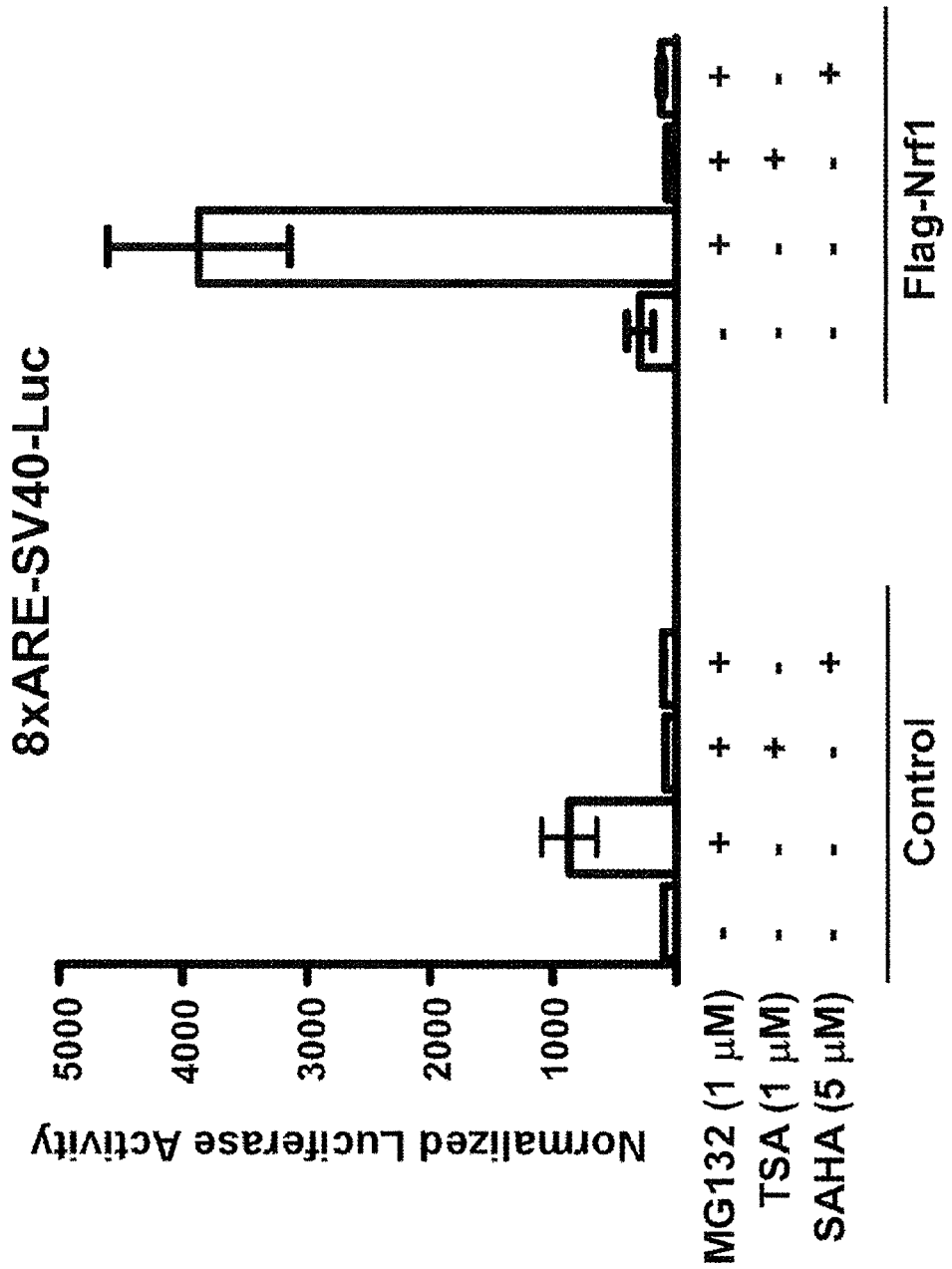
FIG. 10 is a graph of luciferase activity in LNCaP cells transfected with the 8×ARE-SV40 luciferase construct, with Flag-Nrf1, in the presence of MG132, and in combination with TSA or SAHA.

TSA and SAHA were assayed using a luciferase reporter construct. The luciferase reporter was driven by a promoter harboring multimerized anti-oxidant response elements (8×AREs) and was transfected into LNCaP cells. Upon addition of MG132, luciferase expression was increased compared to non-test (untreated) cells, and upon addition of TSA or SAHA in combination with MG132, basal levels of luciferase activity were observed (FIG. 10).

In general, any suitable reporter construct can be utilized for this Nrf1 inhibitor screening assay. For example, a cell line is transfected with an ARE-construct vector—i.e. a construct vector containing at least one ARE sequence. The ARE sequence can be any ARE sequence obtained through computational analysis as described (Wang et al., 2007). The construct vector can have multiple copies of the ARE sequence that activates a promoter. Any suitable promoter can be used, for example, SV40 or TK (thymidine kinase). The readout that is activated by the promoter can be any protein that can be detected. An example of a detectable readout protein is the bioluminescent luciferase, or any other bioluminescent protein. A fluorescent protein or a protein/peptide fused to a fluorescent protein could also be a reporter protein in this ARE-construct. Fluorescent proteins useful as a detectable label include green fluorescent protein, yellow fluorescent protein, cyan fluorescent protein, dsRed, or a derivative thereof (Smith, 2007, *Nature Methods*, 4, 755-761). A fusion protein could also include an antibody epitope (e.g. FLAG, HA, c-Myc, HIS) or a peptide sequence that binds an optically active molecule (e.g. tetracysteine peptide sequence that binds to Lumio™-Green (Invitrogen).

According to an embodiment of the present invention, a reporter construct containing at least one ARE element, a promoter and a reporter protein is transfected into a stable cell line. The transfected cells are then provided a proteasome inhibitor (e.g. MG132, YU101, bortezomib, carfilzomib, etc), and these inhibited transfected cells are divided into a test group and a non-test group, wherein the test group of cells contact a compound or compounds to be assayed.

While the exemplified compounds, TSA and SAHA, were selected based on their known characteristics, alternatively a library of compounds could be screened using this disclosed reporter assay. A test agent (compound) screened using a reporter construct assay according to a method of the invention can be any type of compound including, for example, a peptide, a peptide derivative, a peptoid, a peptidomimetic, a polynucleotide, a polynucleotide derivative, or a small organic molecule. Furthermore, the test agent can be one of a library of test agents, for example, a combinatorial library, which can be a combinatorial library of random test agents, biased test agents, or variegated test agents Inhibition using a proteasome inhibitor will increase expression of the ARE-dependent reporter protein. Any test agent (compound or compounds) that inhibits this ARE-dependent reporter protein is a potential inhibitor of an Nrf1 gene product.

In another embodiment, a stable cell line is transfected with an ARE reporter construct as described, and a population of these transfected cells are also transfected with a vector that overexpresses a tagged Nrf1 protein (or a tagged Nrf1 gene product). Both populations of cells are incubated with a proteasome inhibitor and each population of cells is then divided into a test group and a non-test group, wherein the test group contacts (i.e. is exposed to, is incubated with) a test agent(s). A decrease in reporter protein expression in the test group indicates the test agent inhibits the ARE-dependent reporter protein expression that was induced by the proteasome inhibitor. If the reporter protein expression is enhanced in the cells overexpressing Nrf1, and this reporter protein expression is decreased upon contact with a test agent(s), then the test agent is an inhibitor of Nrf1-dependent ARE transcription. In one embodiment, the cell line transfected with an ARE-reporter construct can be grown in multi-well plates and assayed as described herein using any library of compounds in a high-throughput screen. Methods for high-throughput screens in mammalian cells are known in the art (Fan and Arduengo, 2008, *Cell Notes*, Issue 20, Promega Corporation).

In another embodiment, a screen for an Nrf1 inhibitor is carried out by measuring the endogenous levels of Nrf1 expression in a cell line incubated with a proteasome inhibitor and a test compound or compounds or a library of compounds.

In one embodiment, a method of identifying an inhibitor of NFE2L1 gene product activity in mammalian cells includes contacting the mammalian cells with a proteasome inhibitor, and contacting the mammalian cells with a test compound; and measuring levels of expression and/or synthesis from the NFE2L1 gene locus. Protein expression is measured by any suitable method known in the art, e.g Western blot/Immunoblot analysis. Gene synthesis (levels of mRNA expression) can be measured by any suitable method, e.g. Northern blot analysis.

In a third aspect of the present invention, a method of inhibiting proteasome expression and synthesis is provided using a covalent proteasome inhibitor. In one embodiment of the present invention, induced proteasome synthesis is prevented and enhanced apoptosis is induced in mammalian cells by administering a covalent proteasome inhibitor in combination with an inhibitor of Nrf1 activity to mammalian cells, as shown in FIGS. 11A-11D. A covalent (i.e. irreversible) proteasome inhibitor includes any proteasome inhibitor that binds to the proteasome and does not readily dissociate. Carfilzomib and YU101 are irreversible inhibitors. (See Example 7 and Material and Methods.)

Figure 11A:
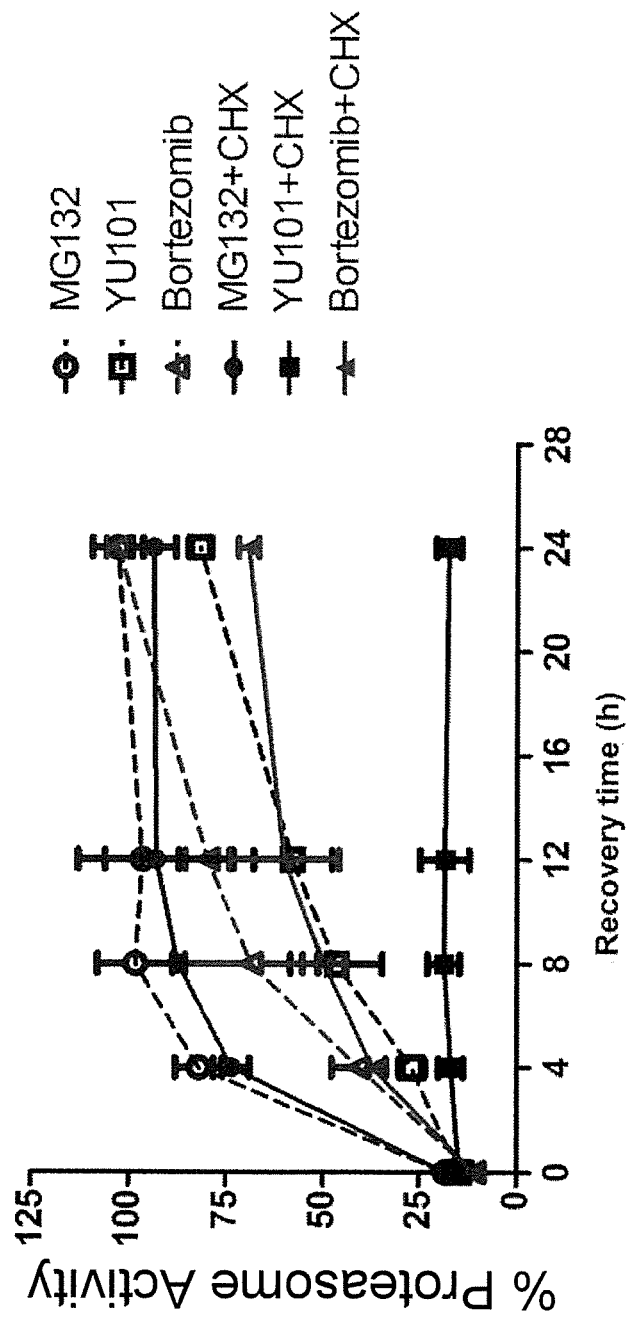
FIGS. 11A-11B are graphs of proteasome activity recovery over time in cells after proteasome inhibition; 11A shows proteasome activity recovery in HT29 cells after inhibition with MG132, YU101, and Bortezomib, in the presence of cyclohexamide; 11B shows proteasome activity recovery in WT and Nrf1–/– MEFs in the presence of MG132 or YU101.
Figure 11B:
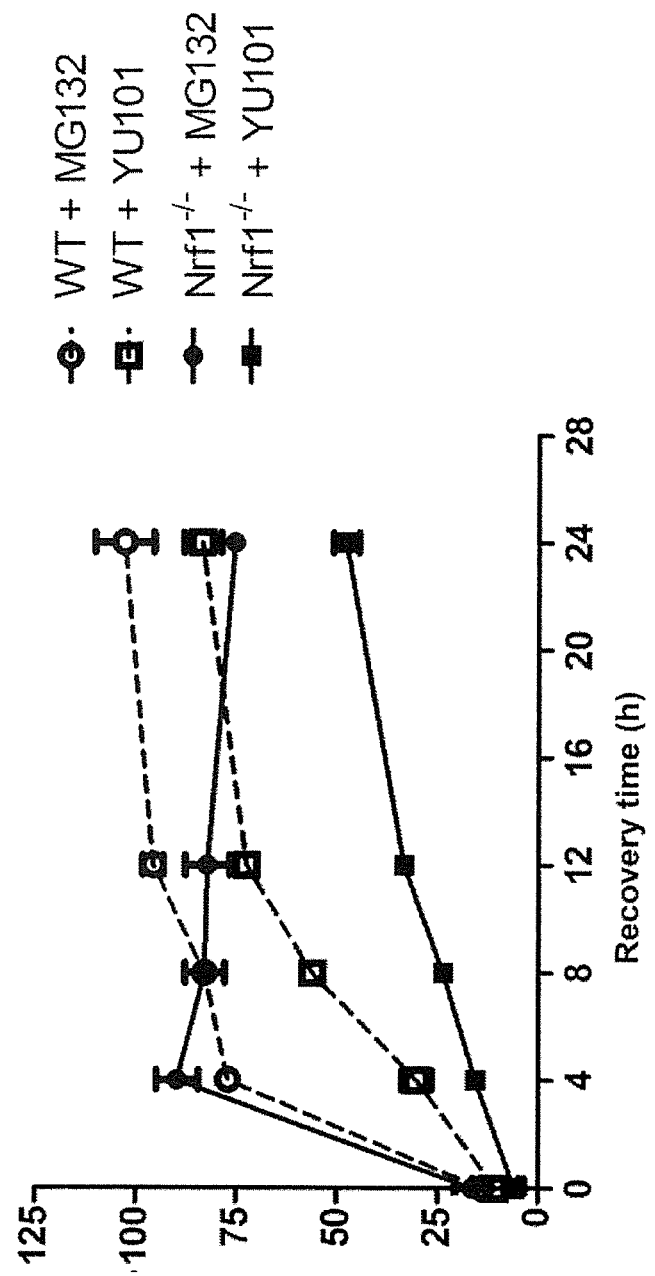

Specifically, HT29 colon cancer cells were exposed to three different proteasome inhibitors—MG132, YU101, and bortezomib—each dosed to achieve 80-90% inhibition of the chymotryptic site. As shown, the proteasome activity recovered after drug wash-out in all of these cases as expected, although with different kinetics (FIG. 11A, hatched lines), presumably dictated by the speed of dissociation of the agent from the active site of the proteasome. However, when the same experiment was performed in the presence of the protein synthesis inhibitor cycloheximide, it was observed that, whereas MG132- and bortezomib-treated cells were still able to recover, YU101-treated cells failed to reinstate their proteasome activity (FIG. 11A, solid lines). Accordingly, new protein synthesis is absolutely required for the recovery of proteasome activity that follows proteasome inhibition elicited by irreversible agents. To this end, WT and Nrf1$^{-/-}$ MEFs were compared in their ability to recover after a transient exposure to MG132 (non-covalent) or YU101 (covalent). Whereas the WT MEFs were able to recover from both types of inhibitors, the Nrf1$^{-/-}$ MEFs were impaired in their ability to recover when treated with YU101 (FIG. 11B). Accordingly, the Nrf1 further enhances the inhibitory and apoptotic effects of a covalent proteasome inhibitor.

In an example of an embodiment of the present invention, mRNA from the Nrf1 activity is inhibited using shRNA targeting a selected sequence of Nrf1 (SEQ ID NO: 1) in mammalian cells inhibited with a covalent proteasome inhibitor. Specifically, shRNA was transfected in MDA-MB-231 breast cancer and U2OS osteosarcoma cell lines in the presence and absence of two concentrations of YU101. Depletion of Nrf1 with shRNA sensitized both cell types to killing by YU101, and this effect was blunted by co-treatment with the pan-caspase inhibitor Z-VAD-FMK (an inhibitor of apoptosis) (FIG. 11C). Additionally, YU101 treatment elicited an enhanced level of cleaved caspase-3 in Nrf1-depleted cells (FIG. 11D), thereby indicating an increase in apoptosis.

While proteasome activity occurs in all mammalian cells, it is understood from the disclosure herein that methods for enhancing proteasome inhibition are more effective in a cancer cell that depends on proteasome activity. As such, some embodiments of the present invention relate to cancers in which the proteasome is found to be overproduced. It has been observed that hematopoietic malignant tumor cells had higher levels of proteasome as well as PSM mRNA levels when compared to peripheral blood mononuclear cells (Kumatori et al., 1990, *Proc. Nat. Acad. Sci.*,). Increased levels of proteasome activity are defined herein to be an increase in mRNA of a PSM gene in a cell compared to peripheral blood mononuclear cells. Ovarian and breast cancer tissues have been reported to exhibit higher levels of proteasome content and activity (Bazzaro et al., 2006 *Cancer Res.*, 66, 3754-3763; Chen and Madura, 2005, *Cancer Res.*, 65, 5599-5606).

EXAMPLES

Materials and Methods and primers (Tables 1 and 2) follow the Examples.

Example 1

Proteasome Inhibitors Induce Proteasome Synthesis in Human Cancer Cells

Figure 1A:
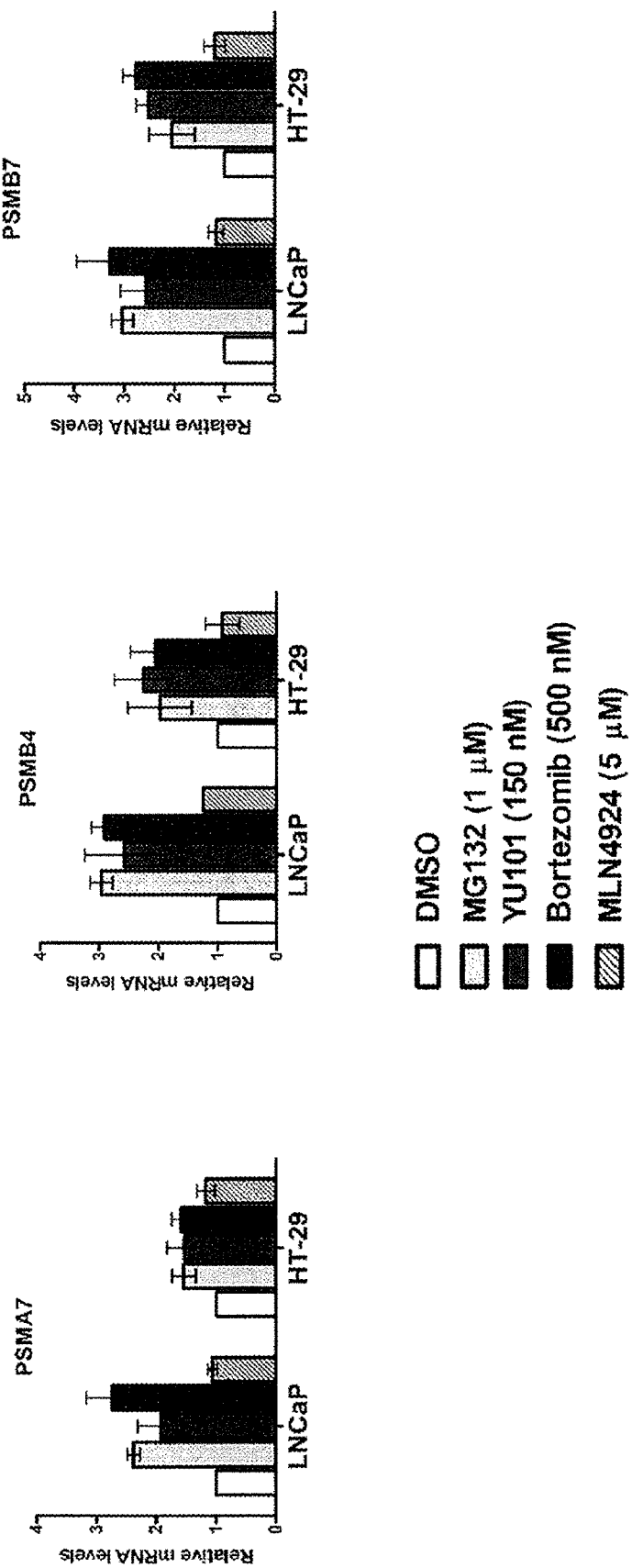
FIGS. 1A-1C show the relative mRNA levels in representative proteasome genes and the NQO1 gene in LNCaP and HT-29 cells incubated with proteasome inhibitors (MG132, YU101 and Bortezomib) and MLN4924.
Figure 1B:
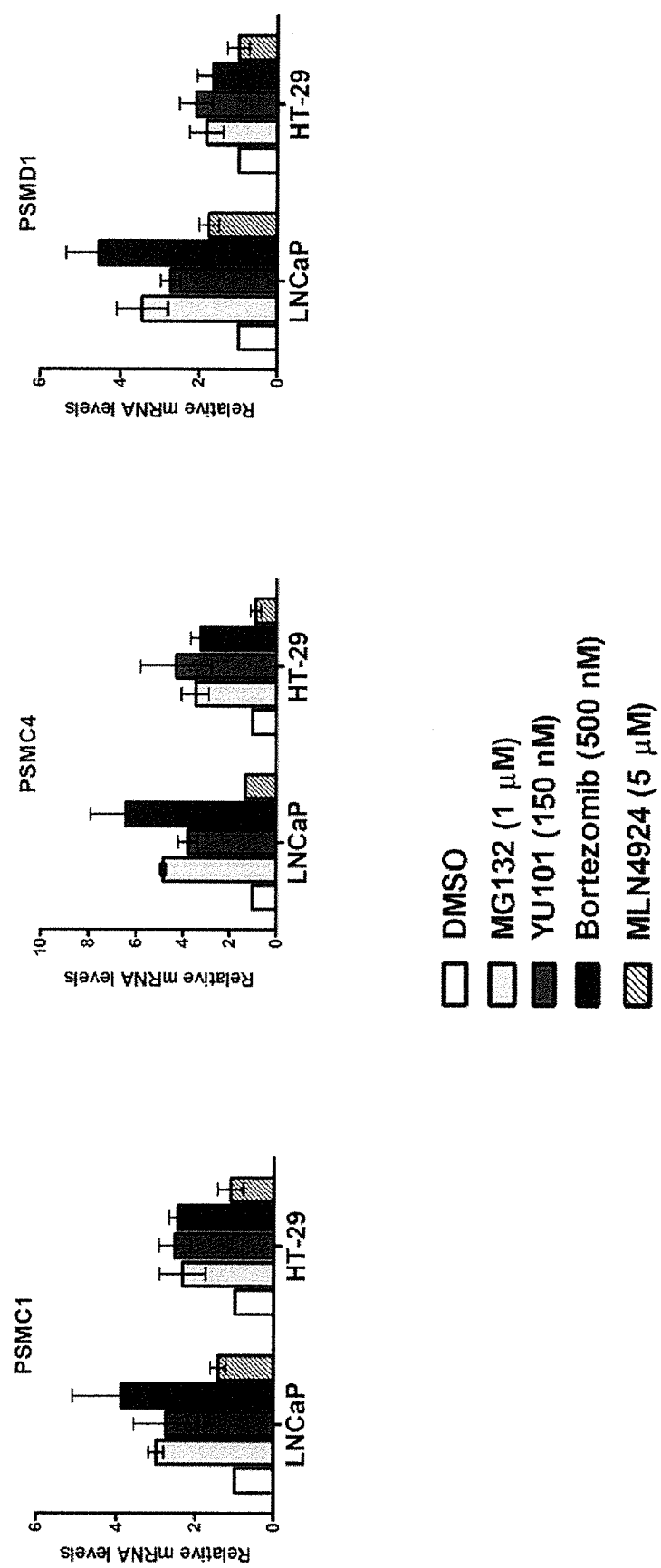
Figure 1C:
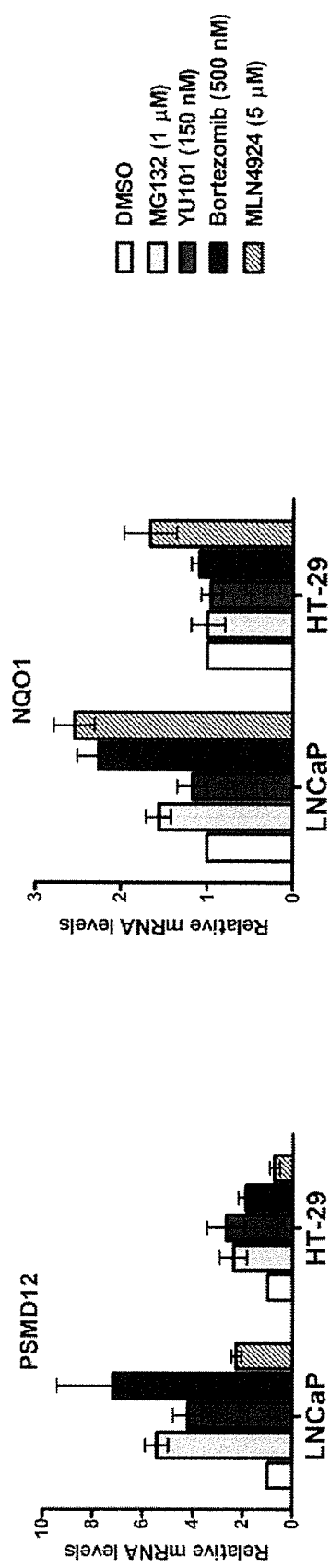

The human prostate cancer LNCaP and colon cancer HT29 cell lines were incubated with different proteasome inhibitors (MG132, YU101, and bortezomib) or the Nedd8 pathway inhibitor MLN4924 (Soucy et al., 2009, *Nature*, 458, 732-736). Prostate cancer LNCaP and colon cancer HT-29 cells were treated with the indicated concentrations of proteasome inhibitors (MG132, YU101, and Bortezomib) or the Nedd8 pathway inhibitor (MLN4924) for 10 hrs, and mRNA levels of representative PSM genes were analyzed by quantitative RT-PCR (FIGS. 1A-1C). The values were normalized to GAPDH and for each cell line the DMSO treated sample was set to 1. Error bars denote SD (n=3). As shown in FIGS. 1A-1C, the proteasome inhibitors were able to robustly induce mRNA levels of several PSM genes that encode members of both the 20S (PSMA7, PSMB4, and PSMB7) and 19S (PSMC1, PSMC4, PSMD1, and PSMD12) complexes, albeit to varying degrees in the two cell lines that were surveyed. MLN4924 works by inhibiting the Nedd8-activating enzyme, the result of which is the accumulation of cullin-RING ligase (CRL) substrates (Soucy et al., 2009). Treatment of cells with MLN4924 stabilizes the transcription factor Nrf2 (Soucy et al., 2009), which should lead to activation of its downstream target genes, as observed for NQO1, a prototypical target gene of Nrf2 (FIG. 1C). In contrast, under the same treatment conditions, MLN4924 failed to appreciably induce the PSM genes in these cell lines (FIGS. 1A-1C), suggesting that inhibition of Nedd8 pathway alone is insufficient to elicit the bounce-back response.

Example 2

Nrf1 is Required for Proteasome Synthesis

Nrf2 has been reported to induce proteasome activity in response to MG132 (Kraft et al., 2006, *Ann. N Y Acad. Sci.*, 1067, 420-424), suggesting that Nrf2 mediates the bounce-back response. To test this hypothesis, mouse embryonic fibroblasts (MEFs) were derived from Nrf2$^{-/-}$ mice (Chan et al., 1996, *Proc. Nat. Acad. Sci.*, 93, 13943-13948). Whereas the wild-type (WT) MEFs accumulated Nrf2 protein after MG132 treatment, Nrf2$^{-/-}$ cells, as expected, did not show any detectable levels of the protein under the same conditions (FIG. 2A), thereby confirming the identity of these cells. Importantly, MG132 induced mRNA levels of PSM genes in both WT and Nrf2$^{-/-}$ MEFs to a similar extent, thus ruling out an essential role for Nrf2 in eliciting the bounce-back response in these cells (FIG. 2B). However, MEFs that are functionally deficient in the related transcription factor Nrf1 (Chan et al., 1998), were severely blunted in their ability to upregulate PSM genes in response to MG132 treatment (FIG. 2B). Accordingly, Nrf1, but not Nrf2 enables enhanced proteasome mRNA accumulation in MEFs treated with proteasome inhibitor.

Specifically, MEFs of different genotypes (WT, Nrf1$^{-/-}$, and Nrf2$^{-/-}$) were treated for 10 hrs with MG132 as indicated (FIG. 2A), and the cell lysates were used for immunoblotting to detect protein levels of Nrf1 (with the antibody raised against the N-terminus) and Nrf2. β-actin protein levels were used as loading control. RNA from MEFs under the same treatment conditions as above was used for quantitative RT-PCR to assess the mRNA levels of representative PSM genes (FIGS. 2B-2C), The values were normalized to GAPDH and the DMSO treated WT sample was set to 1. Error bars denote SD (n=3).

Example 3

Exogenous Nrf1 Restores Nrf1$^{-/-}$ MEFs

Figure 3A:
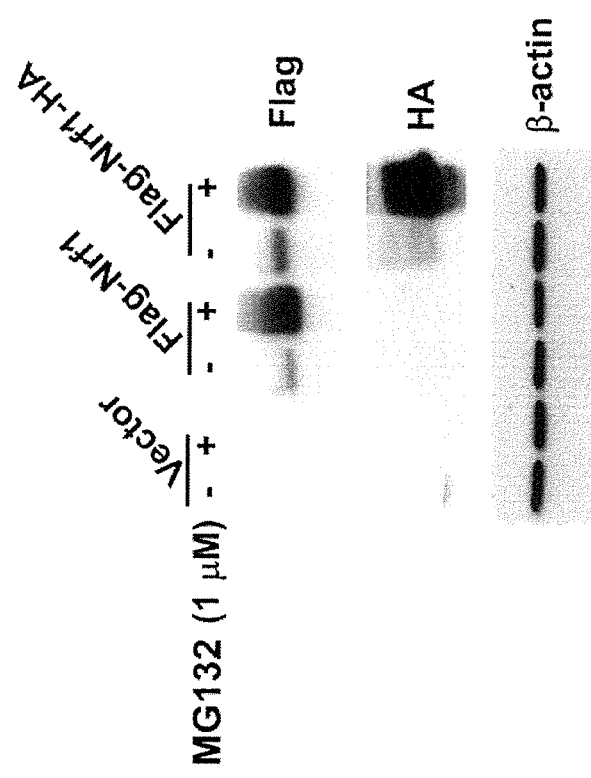
FIGS. 3A-3B show data of Nrf1–/– cells expressing tagged Nrf1; 3A shows a Western blot of Nrf1–/– cells expressing Flag-Nrf1 and Flag-Nrf1-HA; 3B are graphs of the relative mRNA levels of proteasome genes in Nrf1–/– cells with Flag-Nrf1 and Flag-Nrf1-HA in the presence of MG132.
Figure 3B:
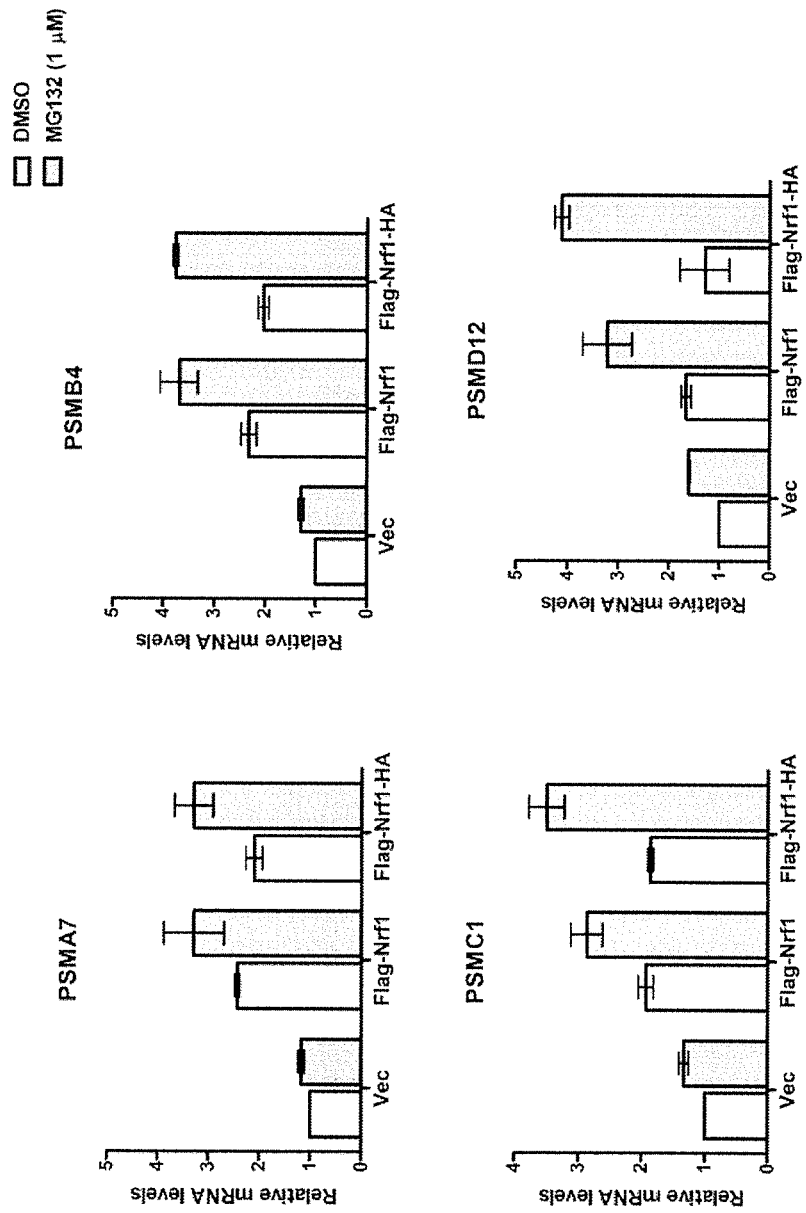

Singly tagged (Flag-Nrf1) and doubly tagged (Flag-Nrf1-HA) retroviral expression constructs and transiently overproduced these tagged proteins by infection of Nrf1$^{-/-}$ MEFs (FIG. 3A). Nrf1$^{-/-}$ MEFs overexpressing tagged Nrf1, but not the vector control cells, upregulated mRNA levels of multiple PSM genes upon MG132 treatment (FIG. 3B). Also, overexpression of tagged-Nrf1 induced PSM mRNA levels in untreated Nrf1$^{-/-}$ cells by ~1.5-2.0 fold compared to vector control (FIG. 3B).

Nrf1$^{-/-}$ MEFs were transduced with retrovirus expressing one of Flag-Nrf1, Flag-Nrf1-HA or vector control and 72 hrs later treated with MG132 for 10 hrs as indicated. The cell lysates were used for immunoblotting to detect the levels of exogenous Nrf1 by using tag-specific antibodies (FIG. 3A). β-actin protein levels were used as loading control. RNA from Nrf1$^{-/-}$ MEFs under the same viral transduction and treatment conditions as above was used for quantitative RT-PCR to assess the mRNA levels of representative PSM genes (FIG. 3B). The values were normalized to GAPDH and the vector-transduced DMSO-treated sample was set to 1. Error bars denote SD (n=3).

Example 4

RNAi Knock Down of Nrf1 Abolishes PSM Gene Upregulation

The Nrf1$^{-/-}$ MEFs retain the expression of a truncated form of the protein as shown in FIG. 2A, as was described originally (Chan et al., 1998). RNAi experiments with a retrovirus that expressed an shRNA targeted to the 5' end of the Nrf1 mRNA were carried out to eliminate the possibility that the truncated Nrf1 protein did not have dominant-negative activity. Knock-down of Nrf1 in WT MEFs (FIG. 4A) mimicked the Nrf1$^{-/-}$ phenotype, in that MG132 did not induce accumulation of proteasome mRNAs in depleted cells (FIG. 4B). Moreover, depletion of the truncated Nrf1 species in Nrf1$^{-/-}$ cells did not revert the proteasome expression defect of these cells ruling out the possibility that the truncated polypeptide could be acting as a dominant-negative.

WT and Nrf1$^{-/-}$ MEFs were transduced with retrovirus expressing sh-Nrf1 or vector control and 72 hrs later treated with MG132 for 10 hrs as indicated. The cell lysates were then used for immunoblotting to analyze protein levels of Nrf1 with either a rabbit polyconal antibody specific for the N-terminus or a mouse polyclonal antibody specific for the C-terminal region of Nrf1 (FIG. 4A). β-actin protein levels were used as loading control. RNA from MEFs under the same viral transduction and treatment conditions as above was used for quantitative RT-PCR to assess the mRNA levels of representative PSM genes (FIG. 4B). The values were normalized to GAPDH and for each cell line the vector-transduced DMSO-treated sample was set to 1. Error bars denote SD (n=3).

Example 5

Nrf1 Activates AREs of PSM Genes

Sequence alignment of the genomic region close to the transcription start site (indicated by +1) of the PSMB6 gene in mouse and human. The putative ARE sequences and the start codon are marked as shown (FIG. 6). WT and Nrf1$^{-/-}$ MEFs were transfected with the PSMB6-Luc construct and 24 hrs post-transfection, the cells were treated with the indicated concentration of MG132 for 12 hrs after which luciferase assays were performed as described herein (FIG. 7). Error bars denote SD (n=3). FIG. 8 shows a schematic representation of the luciferase reporter constructs—3× PSMA4-ARE-Luc which has three copies of ARE derived from the first intron of the human PSMA4 gene and 3×PSMA4-mutARE-Luc which is identical to the above except that it has the AREs mutated in key positions indicated by asterisks. LNCaP cells were transiently transfected with the indicated reporter constructs along with either a vector control or Flag-Nrf1 expression construct. Forty-eight hours (hrs) after transfection, the cells were further incubated with the indicated concentration of MG132 for 12 hrs after which luciferase assays were performed as described herein (FIG. 9). Error bars denote SD (n=3).

Example 6 Reporter Assay Using TSA and SAHA. This reporter assay was prepared utilizing an in silico search for agents that antagonize the proteasome bounce-back response. Specifically, "Connectivity Map", (Lamb et al. 2006, *Science* 313, 1929-1935), an online resource that holds a collection of gene expression profiles obtained from human cells treated with a large number of small molecules, was used to generate a list of compounds having genomic signatures corresponding to the ability to downregulate the expression of numerous PSM genes. From this list of compounds, select compounds were tested using quantitative RT-PCR.

LNCaP cells were subjected to treatment with one of MG132 (1 µM), TSA (1 µM), SAHA (5 µM), MG132 (1 µM)+TSA (1 µM), or MG132 (1 µM)+SAHA (1 µM) for 10 hrs and the RNA from these cells was used for quantitative RT-PCR to assess the mRNA levels of representative PSM genes (FIG. 5A). The values were normalized to GAPDH and the DMSO-treated sample was set to 1. A representative experiment performed in duplicates is shown. MDA-MB-231 cells were treated with different agents at the same concentrations as above (except MG132 which was used at 5 µM) for 48 hrs after which the cells were used for cell-titer glo assay to assess cell viability. Data from an experiment performed in quadruplicates is shown (FIG. 5B). LNCaP cells transfected with 8×ARE-SV40-Luc construct alone (control) or co-transfected with Flag-Nrf1 were further treated with different agents as indicated (FIG. 10). pRL-TK renilla luciferase expression construct was used as a transfection control for normalization. Sixteen hours later, the cells were harvested and used for Luciferase assay.

Example 7

Nrf1 Increases Cancer Cell Apoptosis after Proteasome Inhibition

Figure 12A:
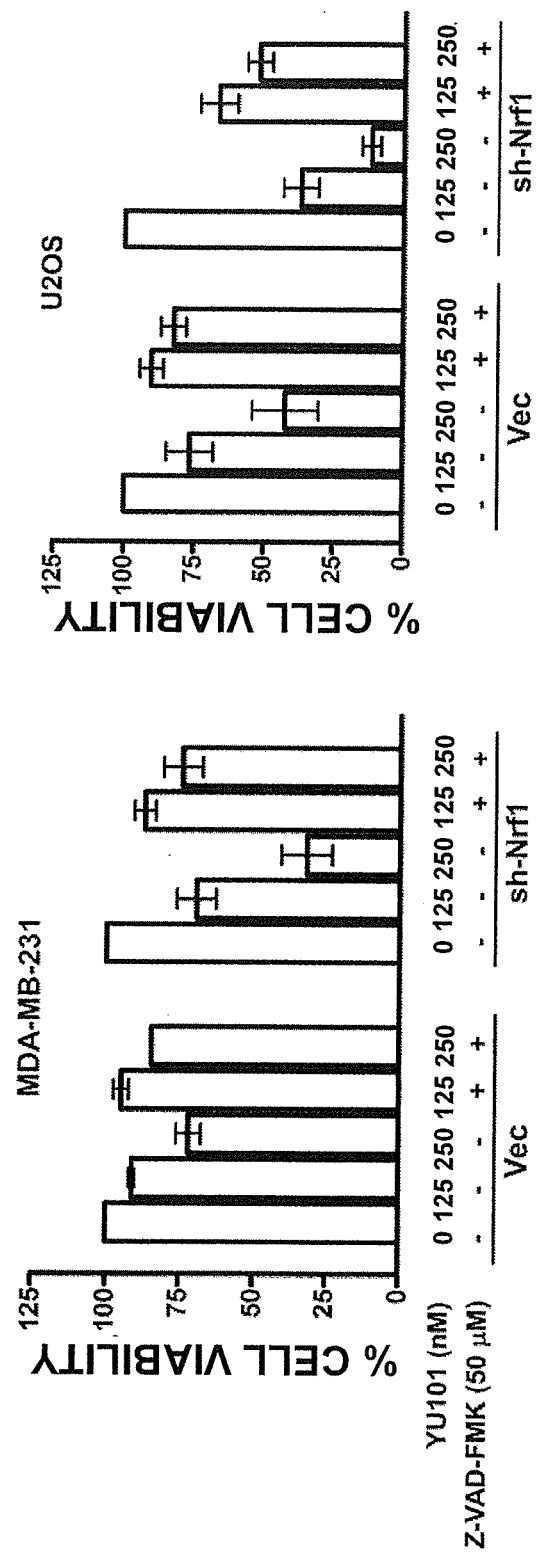
FIGS. 12A-12B show data from apoptosis assay using YU101 and sh-Nrf1; 12A shows graphs of cell viability in MDA-MB-231 and U20S cells inhibited with YU101 and sh-Nrf1 in the presence of Z-VAD-FMK; 12B shows Western blot of Nrf1 and caspase-3 protein in MDA-MB-231 and U2OS cells.
Figure 12B:
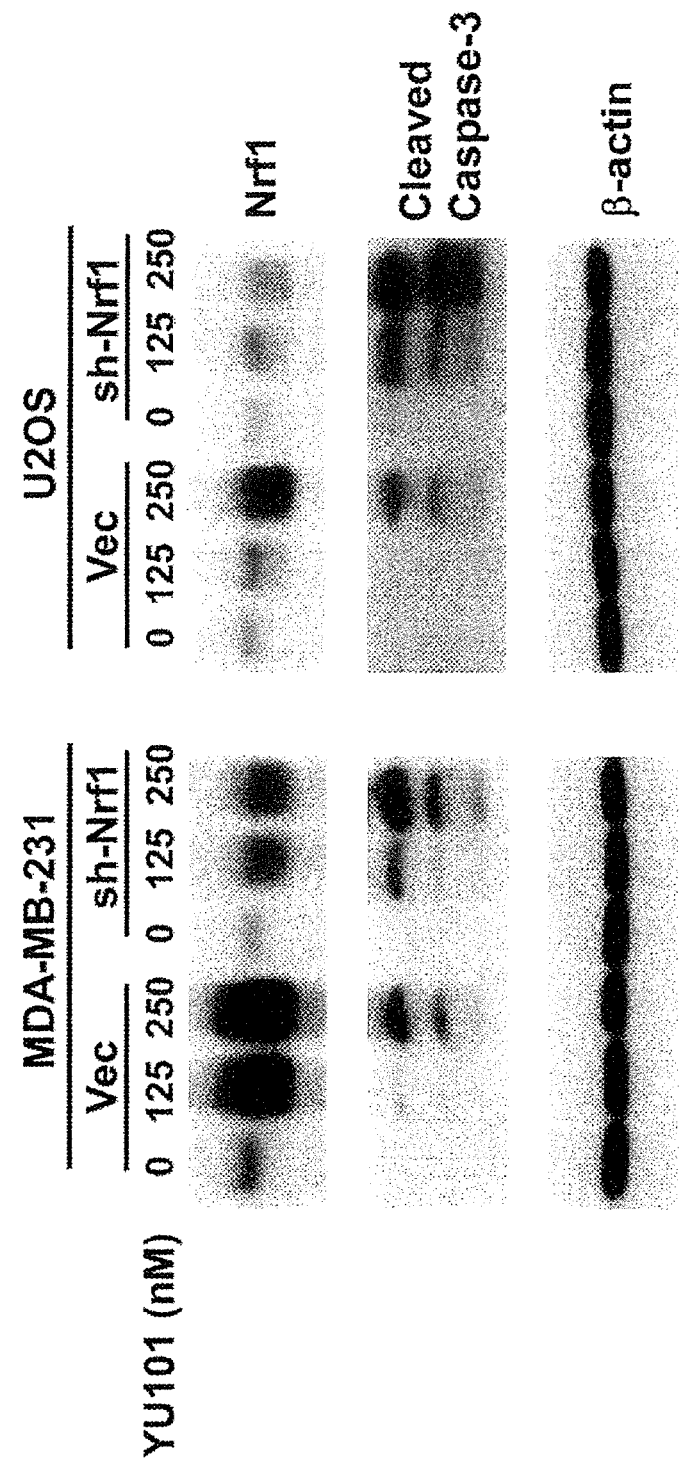

HT29 cells were treated with either MG132 (2 µM), YU101 (100 nM) or Bortezomib (40 nM) for 1 hr after which the drugs were washed off and the cells were allowed to recover in the absence or presence of 50 µg/ml cycloheximide (CHX) (FIG. 11A). Cells were frozen at different time points as indicated and were used for proteasome activity assays as described herein. For each time point, the results are normalized to DMSO-treated control in the case of hatched lines and to CHX-treated control in the case of solid lines. Error bars denote SD (n=3). WT and Nrf1$^{-/-}$ MEFs were treated with either MG132 (50 µM) or YU101 (300 nM) for an hour after which the drugs were washed off and proteasome activity was measured for cells collected at different time points as indicated (FIG. 11A). For the YU101 treatments, a single-phase exponential curve fit estimates that the time taken to recover half of the inhibited activity was 6.92±1.64 hrs and 15.96±5.49 hrs respectively for the WT and Nrf1$^{-/-}$ MEFs. The results were normalized to DMSO-treated control for each cell type. Error bars denote S.E.M. (n=2). MDA-MB-231 and U2OS cells were transduced with retrovirus expressing either sh-Nrf1 or vector control, and 48 hrs later were seeded in to 96-well plates. The next day, the cells were treated with indicated concentrations of YU101 and the pan-caspase inhibitor Z-VAD-FMK, and further incubated for 72 hrs. The cell viability was then assessed using the CellTiter-Glo method (FIG. 12A). The results were normalized to DMSO-treated control which was set to 100% in each case. Error bars denote S.E.M. (n=2). MDA-MB-231 and U2OS cells were transduced with retrovirus expressing either sh-Nrf1 or vector control, and 72 hrs later were treated with indicated concentrations of YU101 for 48 hrs (MDA-MB-231) or 24 hrs (U205) (FIG. 12B). The cell lysates were used for immunoblotting to detect the levels of Nrf1 (with the antibody raised against N-terminus) and cleaved caspase-3. β-actin protein levels were used as loading control.

Materials and Methods

Constructs/Primers.

The coding region of human Nrf1 was amplified from a full-length cDNA-containing plasmid (Open Biosystems) using primers 5'-CAC TCA CTG CGG CCG CT C TTT CTC TGA AGA A AT ACT TAA CGG AA-3' (forward) (SEQ ID NO: 5) and 5'- TCA CTT TCT CCG GTC CTT TGG C-3' (reverse) (SEQ ID NO: 6), digested with NotI and cloned in-frame in to the NotI-HpaI site of the pMSCV-hyg retroviral vector (Clontech) that was previously modified to encode an N-terminal 3×FLAG tag, resulting in the construct Flag-Nrf1 (RDB-2411). The construct Flag-Nrf1-HA (RDB-2412) was obtained as above except that the reverse primer (5'-TCA GGC GTA GTC GGG CAC GTC GTA GGG GTA CTT TCT CCG GTC CTT TGG C-3') (SEQ ID NO: 7) encoded an HA tag sequence.

The shRNA expression construct shNrf1 (RDB-2413) targeting Nrf1 was based on a 19-mer sequence (GGGAT-TCGGTGAAGATTTG) (SEQ ID NO:1) present in the coding region of both human and mouse genes and was cloned in to pSUPER.retro.puro (Oligoengine).

To obtain 3×PSMA4-ARE-Luc (RDB-2415), an oligo (5'-cgagccgtgggcacga TGACTCTGCA ccgcctcctctgagc-cgtgggcacga TGACTCTGCA ccgcctcctctgagccgtgggcacga TGACTCTGCA ccgcctcctctg-3') (SEQ ID NO: 8) containing three copies of a putative ARE (shown in upper-case—TGACTCTGCA) (SEQ ID NO: 4) derived from the first intron of the human PSMA4 gene was annealed to its corresponding reverse-complement oligo and cloned into pGL3-promoter vector (Promega). The construct 3×PSMA4-mutARE-Luc (RDB-2416) was obtained as above except that the putative AREs were modified to TGACTCTAAA, (SEQ ID NO: 9) where the mutation is shown underlined. To obtain the PSMB6-Luc construct, the ~3 kb promoter region of the mouse PSMB6 gene was amplified using primers 5'-TGA TGG CTC ATC GCC ATC CAT-3' (forward) (SEQ ID NO: 10) and 5'-GGC CGC CAT CTT CCT CTG CTA-3' (reverse) (SEQ ID NO: 11) from mouse genomic DNA and cloned in to pGL3-Basic vector (Promega).

Cell Culture and Retroviral Transductions.

Prostate cancer LNCaP, colon cancer HT29, breast cancer MDA-MB-231, osteosarcoma U2OS, and 293T cells were grown in Dulbecco's modified Eagle's medium (DMEM) supplemented with 10% fetal bovine serum (Atlanta Biologicals), penicillin and streptomycin (Invitrogen) at 37° C. in 5% $CO_2$. Mouse embryonic fibroblasts (MEFs) were grown as above except that the medium was additionally supplemented with β-mercaptoethanol and non-essential amino acids (Invitrogen). Primary MEFs derived from knock-out animals were used in FIG. 2 and for all subsequent experiments, MEFs immortalized with an shRNA construct (RDB-2418; a kind gift from Dr. Mei-Ling Kuo, City of Hope, Duarte, Calif.) targeting p19ARF and selected for puromycin resistance were used.

For retroviral production, 293T cells were transfected with the required retroviral construct along with helper plasmids. Forty-eight hours after transfection, media supernatant containing the retrovirus was collected every 4-5 hrs for two days. This retrovirus-containing medium, supplemented with polybrene (10 μg/ml), was used to transduce the target cells.

Quantitative Reverse Transcription PCR (RT-PCR).

RNA was isolated using the RNeasy kit (Qiagen). cDNA was prepared using the Superscript III first strand synthesis kit (Invitrogen) according to the manufacturer's recommendations. Quantitative PCR (qPCR) was performed using the SYBR GreenER supermix (Invitrogen). Primers used in these qPCRs are listed in Tables 1 and 2.

Immunoblot Analysis.

Cells were lysed in RIPA buffer (50 mM Tris pH 7.4, 150 mM NaCl, 1% NP40, 1% Na. Deoxycholate, 0.1% SDS, 1 mM EDTA) supplemented with protease and phosphatase inhibitor cocktail (Pierce). For detecting Nrf1, either a rabbit polyclonal antibody raised against the N-terminus (Chan et al., 1998) or a mouse polyclonal antibody specific for the C-terminus (Novus Biologicals) was used. Other immunoblots were performed with antibodies specific for Nrf2 (SantaCruz Biotechnology), Flag tag (Sigma-Aldrich), HA tag (Roche Diagnostics), cleaved caspase-3 (Cell Signaling), and β-actin (Sigma-Aldrich).

Luciferase Assays.

Cells were transiently transfected with the firefly (promoter reporters) and renilla luciferase (pRL-TK; Promega) constructs along with effector plasmid as required. After harvesting the cells, luciferase assays were performed using the Dual Luciferase reporter assay system (E1910; Promega) according to the instructions from the manufacturer. The firefly luciferase activity was normalized to renilla luciferase activity for all experiments.

Proteasome Activity Recovery Assays.

Cells seeded in 96-well plates were treated with different proteasome inhibitors for an hour at concentrations determined to inhibit proteasome activity by 80-90%. The cells were then washed with PBS thrice and allowed to recover in fresh medium. At definite time points, the cells were freeze-thawed in TE buffer (20 mM Tris pH 8, 5 mM EDTA) and subsequently used for measuring proteasome activity as described previously (Demo et al., 2007).

Cell Viability Assays.

Cells in 96-well plates were treated with different agents as required and cell viability was assessed using the Cell-Titer Glo kit (G7572; Promega) according to the protocol recommended by the manufacturer. By employing a luminescence read-out, this kit quantifies the level of ATP which is proportional to the number of viable cells.

Table 1

The following human-specific primers were used for quantitative RT-PCR experiments.

| Gene | Forward Primer | Reverse Primer |
| --- | --- | --- |
| PSMA7 | 5'-CTGTGCTTTGGATGACAACG-3' (SEQ ID NO: 12) | 5'-CGATGTAGCGGGTGATGTACT-3' (SEQ ID NO: 13) |
| PSMB4 | 5'-CTCGTTTCCGCAACATCTCT-3' (SEQ ID NO: 14) | 5'-TGTCCATCTCCCAGAAGCTC-3' (SEQ ID NO: 15) |
| PSMB7 | 5'-TGCAAAGAGGGGATACAAGC-3' (SEQ ID NO: 16) | 5'-GCAACAACCATCCCTTCAGT-3' (SEQ ID NO: 17) |
| PSMC1 | 5'-TTCCGAGTTGCTGAAGAACA-3' (SEQ ID NO: 18) | 5'-ATCCATCCAACTGGTTCAGC-3' (SEQ ID NO: 19) |
| PSMC4 | 5'-GGAAGACCATGTTGGCAAAG-3' (SEQ ID NO: 20) | 5'-AAGATGATGGCAGGTGCATT-3' (SEQ ID NO: 21) |
| PSMD1 | 5'-GGGGACCTCTTCAATGTCAA-3' (SEQ ID NO: 22) | 5'-GCCTTCCAATCTCTGGTCAA-3' (SEQ ID NO: 23) |
| PSMD12 | 5'-GTGCGCGACTGACTAAAACA-3' (SEQ ID NO: 24) | 5'-TAGGCAGAGCCTCATTTGCT-3' (SEQ ID NO: 25) |
| NQO1 | 5'-AGCCCAGATATTGTGGCTGA-3' (SEQ ID NO: 26) | 5'-CGGAAGGGTCCTTTGTCATA-3' (SEQ ID NO: 27) |
| GAPDH | 5'-GGTGGTCTCCTCTGACTTCAACA-3' (SEQ ID NO: 28) | 5'-GTTGCTGTAGCCAAATTCGTTGT-3' (SEQ ID NO: 29) |

Table 2

The following mouse-specific primers were used for quantitative RT-PCR experiments.

| Gene | Forward Primer | Reverse Primer |
| --- | --- | --- |
| PSMA7 | 5'-AACGTCTGTATGGCCTTTGC-3' (SEQ ID NO: 30) | 5'-GTCACTGGGTCCTCCACTGT-3' (SEQ ID NO: 31) |
| PSMB4 | 5'-TTCACTGGCCACTGGTTATG-3' (SEQ ID NO: 32) | 5'-CGAACGGGCATCTCTGTAGT-3' (SEQ ID NO: 33) |
| PSMB7 | 5'-CTGTCTTGGAAGCGGATTTC-3' (SEQ ID NO: 34) | 5'-GCAACAACCATCCCTTCAGT-3' (SEQ ID NO: 35) |
| PSMC1 | 5'-AAGGGGGTCATTCTCTACGG-3' (SEQ ID NO: 36) | 5'-AAGCTCTGAGCCAACCACTC-3' (SEQ ID NO: 37) |
| PSMC4 | 5'-TGGTCATCGGTCAGTTCTTG-3' (SEQ ID NO: 38) | 5'-CGGTCGATGGTACTCAGGAT-3' (SEQ ID NO: 39) |
| PSMD1 | 5'-GGGGCTTTTGAGGAGTCTCT-3' (SEQ ID NO: 40) | 5'-GCAAATCTGCATTTTCCACA-3' (SEQ ID NO: 41) |
| PSMD12 | 5'-TCACAGACCTGCCAGTCAAG-3' (SEQ ID NO: 42) | 5'-AGGTTTTAGTCAGCCGAGCA-3' (SEQ ID NO: 43) |
| GAPDH | 5'-AACTTTGGCATTGTGGAAGG-3' (SEQ ID NO: 44) | 5'-GGATGCAGGGATGATGTTCT-3' (SEQ ID NO: 45) |

In summary, methods and compositions for inhibiting Nrf1 activity are provided for enhancing apoptosis in mammalian cells. Apoptosis is enhanced in mammalian cells by co-inhibiting Nrf1 activity and proteasome activity. Methods for identifying Nrf1 inhibitors are provided using an assay for screening Nrf1 inhibitors that enhance proteasome inhibition.

While the present invention has been illustrated and described with reference to certain exemplary embodiments, those of ordinary skill in the art will understand that various modifications and changes may be made to the described embodiments without departing from the spirit and scope of the present invention, as defined in the following claims.

What is claimed is:

1. A method of inducing apoptosis in mammalian cells, comprising:
    contacting the mammalian cells with a proteasome inhibitor; and
    contacting the mammalian cells with an inhibitor of a nuclear factor erythroid-derived 2-related factor-1 (NFE2L1) gene product activity, the inhibitor being an shRNA that targets an mRNA transcript of a 19 base pair DNA coding sequence of NFE2L1 as set forth in SEQ ID NO: 1.

2. A method of preventing or decreasing induced expression of proteasome genes in mammalian cells, comprising:
    contacting the mammalian cells with a proteasome inhibitor; and
    contacting the mammalian cells with an inhibitor of nuclear factor erythroid-derived 2-related factor-1 (NFE2L1) gene product activity, the inhibitor being an shRNA that targets an mRNA transcript of a 19 base pair DNA coding sequence of NFE2L1 as set forth in SEQ ID NO: 1.

3. The method of claim 1 or 2, wherein the NFE2L1 gene product is Nrf1 or TCF11.

4. The method of claim 1 or 2, wherein the proteasome inhibitor is a covalent proteasome inhibitor compound.

5. The method of claim 4, wherein the covalent proteasome inhibitor is carfilzomib.

6. The method of claim 1, wherein the mammalian cells are cancer cells.

7. The method of claim 6, wherein the cancer cells have elevated levels of at least one proteasome gene.

8. The method of claim 6, wherein the cancer cells are selected from the group consisting of hematopoietic cancers, ovarian cancers, and breast cancers.

9. The method of claim 1, wherein the apoptosis is induced to an extent that is greater than would result from contacting the mammalian cells with the proteasome inhibitor alone.

10. The method of claim 2, wherein the induced expression of proteasome genes in mammalian cells is less than would result from contacting mammalian cells with the proteasome inhibitor alone.

11. A method of identifying a compound that inhibits NFE2L1-protein activity in mammalian cells comprising:
    contacting the mammalian cells with a proteasome inhibitor;
    contacting the mammalian cells with a test compound; and
    measuring NFE2L1 protein activity using an antioxidant response element (ARE).

* * * * *

SEQUENCE LISTING

<160> NUMBER OF SEQ ID NOS: 45

<210> SEQ ID NO 1
<211> LENGTH: 19
<212> TYPE: DNA
<213> ORGANISM: Artificial Sequence
<220> FEATURE:
<223> OTHER INFORMATION: NFE2L1 shRNA target

<400> SEQUENCE: 1
gggattcggt gaagatttg                                                       19

<210> SEQ ID NO 2
<211> LENGTH: 10
<212> TYPE: DNA
<213> ORGANISM: Artificial Sequence
<220> FEATURE:
<223> OTHER INFORMATION: PSMB6 putative ARE

<400> SEQUENCE: 2
tgacagagcg                                                                 10

<210> SEQ ID NO 3
<211> LENGTH: 10
<212> TYPE: DNA
<213> ORGANISM: Artificial Sequence
<220> FEATURE:
<223> OTHER INFORMATION: PSMB6 putative ARE

<400> SEQUENCE: 3
tgacggagcg                                                                 10

<210> SEQ ID NO 4
<211> LENGTH: 10
<212> TYPE: DNA
<213> ORGANISM: Artificial Sequence
<220> FEATURE:
<223> OTHER INFORMATION: PSMA4 putative ARE

<400> SEQUENCE: 4
tgactctgca                                                                 10

<210> SEQ ID NO 5
<211> LENGTH: 44
<212> TYPE: DNA
<213> ORGANISM: Artificial Sequence
<220> FEATURE:
<223> OTHER INFORMATION: NRF1 forward primer

<400> SEQUENCE: 5
cactcactgc ggccgctctt tctctgaaga aatacttaac ggaa                            44

<210> SEQ ID NO 6
<211> LENGTH: 22
<212> TYPE: DNA
<213> ORGANISM: Artificial Sequence
<220> FEATURE:
<223> OTHER INFORMATION: NRF1 reverse primer

<400> SEQUENCE: 6
tcactttctc cggtcctttg gc                                                   22

<210> SEQ ID NO 7
<211> LENGTH: 49
<212> TYPE: DNA
<213> ORGANISM: Artificial Sequence

```
<220> FEATURE:
<223> OTHER INFORMATION: NRF1 HA reverse primer

<400> SEQUENCE: 7
tcaggcgtag tcgggcacgt cgtaggggta ctttctccgg tcctttggc                49

<210> SEQ ID NO 8
<211> LENGTH: 110
<212> TYPE: DNA
<213> ORGANISM: Artificial Sequence
<220> FEATURE:
<223> OTHER INFORMATION: PSMA4 oligo

<400> SEQUENCE: 8
cgagccgtgg gcacgatgac tctgcaccgc ctcctctgag ccgtgggcac gatgactctg     60
caccgcctcc tctgagccgt gggcacgatg actctgcacc gcctcctctg                110

<210> SEQ ID NO 9
<211> LENGTH: 10
<212> TYPE: DNA
<213> ORGANISM: Artificial Sequence
<220> FEATURE:
<223> OTHER INFORMATION: PSMA4 mutant ARE

<400> SEQUENCE: 9
tgactctaaa                                                            10

<210> SEQ ID NO 10
<211> LENGTH: 21
<212> TYPE: DNA
<213> ORGANISM: Artificial Sequence
<220> FEATURE:
<223> OTHER INFORMATION: PSMB6 ARE forward primer

<400> SEQUENCE: 10
tgatggctca tcgccatcca t                                               21

<210> SEQ ID NO 11
<211> LENGTH: 21
<212> TYPE: DNA
<213> ORGANISM: Artificial Sequence
<220> FEATURE:
<223> OTHER INFORMATION: PSMB6 ARE reverse primer

<400> SEQUENCE: 11
ggccgccatc ttcctctgct a                                               21

<210> SEQ ID NO 12
<211> LENGTH: 20
<212> TYPE: DNA
<213> ORGANISM: Artificial Sequence
<220> FEATURE:
<223> OTHER INFORMATION: PSMA7 forward primer

<400> SEQUENCE: 12
ctgtgctttg gatgacaacg                                                 20

<210> SEQ ID NO 13
<211> LENGTH: 21
<212> TYPE: DNA
<213> ORGANISM: Artificial Sequence
<220> FEATURE:
<223> OTHER INFORMATION: PSMA7 reverse primer

<400> SEQUENCE: 13
```
cgatgtagcg ggtgatgtac t                                            21

<210> SEQ ID NO 14
<211> LENGTH: 20
<212> TYPE: DNA
<213> ORGANISM: Artificial Sequence
<220> FEATURE:
<223> OTHER INFORMATION: PSMB4 forward primer

<400> SEQUENCE: 14
ctcgtttccg caacatctct                                              20

<210> SEQ ID NO 15
<211> LENGTH: 20
<212> TYPE: DNA
<213> ORGANISM: Artificial Sequence
<220> FEATURE:
<223> OTHER INFORMATION: PSMB4 reverse primer

<400> SEQUENCE: 15
tgtccatctc ccagaagctc                                              20

<210> SEQ ID NO 16
<211> LENGTH: 20
<212> TYPE: DNA
<213> ORGANISM: Artificial Sequence
<220> FEATURE:
<223> OTHER INFORMATION: PSMB7 forward primer

<400> SEQUENCE: 16
tgcaaagagg ggatacaagc                                              20

<210> SEQ ID NO 17
<211> LENGTH: 20
<212> TYPE: DNA
<213> ORGANISM: Artificial Sequence
<220> FEATURE:
<223> OTHER INFORMATION: PSMB7 reverse primer

<400> SEQUENCE: 17
gcaacaacca tcccttcagt                                              20

<210> SEQ ID NO 18
<211> LENGTH: 20
<212> TYPE: DNA
<213> ORGANISM: Artificial Sequence
<220> FEATURE:
<223> OTHER INFORMATION: PSMC1 forward primer

<400> SEQUENCE: 18
ttccgagttg ctgaagaaca                                              20

<210> SEQ ID NO 19
<211> LENGTH: 20
<212> TYPE: DNA
<213> ORGANISM: Artificial Sequence
<220> FEATURE:
<223> OTHER INFORMATION: PSMC1 reverse primer

<400> SEQUENCE: 19
atccatccaa ctggttcagc                                              20

<210> SEQ ID NO 20
<211> LENGTH: 20
<212> TYPE: DNA
<213> ORGANISM: Artificial Sequence

```
<220> FEATURE:
<223> OTHER INFORMATION: PSMC4 forward primer

<400> SEQUENCE: 20
ggaagaccat gttggcaaag                                               20

<210> SEQ ID NO 21
<211> LENGTH: 20
<212> TYPE: DNA
<213> ORGANISM: Artificial Sequence
<220> FEATURE:
<223> OTHER INFORMATION: PSMC4 reverse primer

<400> SEQUENCE: 21
aagatgatgg caggtgcatt                                               20

<210> SEQ ID NO 22
<211> LENGTH: 20
<212> TYPE: DNA
<213> ORGANISM: Artificial Sequence
<220> FEATURE:
<223> OTHER INFORMATION: PSMD1 forward sequence

<400> SEQUENCE: 22
ggggacctct tcaatgtcaa                                               20

<210> SEQ ID NO 23
<211> LENGTH: 20
<212> TYPE: DNA
<213> ORGANISM: Artificial Sequence
<220> FEATURE:
<223> OTHER INFORMATION: PSMD1 reverse sequence

<400> SEQUENCE: 23
gccttccaat ctctggtcaa                                               20

<210> SEQ ID NO 24
<211> LENGTH: 20
<212> TYPE: DNA
<213> ORGANISM: Artificial Sequence
<220> FEATURE:
<223> OTHER INFORMATION: PSMD12 forward primer

<400> SEQUENCE: 24
gtgcgcgact gactaaaaca                                               20

<210> SEQ ID NO 25
<211> LENGTH: 20
<212> TYPE: DNA
<213> ORGANISM: Artificial Sequence
<220> FEATURE:
<223> OTHER INFORMATION: PSMD12 reverse primer

<400> SEQUENCE: 25
taggcagagc ctcatttgct                                               20

<210> SEQ ID NO 26
<211> LENGTH: 20
<212> TYPE: DNA
<213> ORGANISM: Artificial Sequence
<220> FEATURE:
<223> OTHER INFORMATION: NQO1 forward primer

<400> SEQUENCE: 26
agcccagata ttgtggctga                                               20
```

```
<210> SEQ ID NO 27
<211> LENGTH: 20
<212> TYPE: DNA
<213> ORGANISM: Artificial Sequence
<220> FEATURE:
<223> OTHER INFORMATION: NQO1 reverse primer

<400> SEQUENCE: 27
cggaagggtc ctttgtcata                                                  20

<210> SEQ ID NO 28
<211> LENGTH: 23
<212> TYPE: DNA
<213> ORGANISM: Artificial Sequence
<220> FEATURE:
<223> OTHER INFORMATION: GAPDH forward primer

<400> SEQUENCE: 28
ggtggtctcc tctgacttca aca                                              23

<210> SEQ ID NO 29
<211> LENGTH: 23
<212> TYPE: DNA
<213> ORGANISM: Artificial Sequence
<220> FEATURE:
<223> OTHER INFORMATION: GAPDH reverse primer

<400> SEQUENCE: 29
gttgctgtag ccaaattcgt tgt                                              23

<210> SEQ ID NO 30
<211> LENGTH: 20
<212> TYPE: DNA
<213> ORGANISM: Artificial Sequence
<220> FEATURE:
<223> OTHER INFORMATION: PSMA7 forward primer mouse

<400> SEQUENCE: 30
aacgtctgta tggcctttgc                                                  20

<210> SEQ ID NO 31
<211> LENGTH: 20
<212> TYPE: DNA
<213> ORGANISM: Artificial Sequence
<220> FEATURE:
<223> OTHER INFORMATION: PSMA7 reverse primer

<400> SEQUENCE: 31
gtcactgggt cctccactgt                                                  20

<210> SEQ ID NO 32
<211> LENGTH: 20
<212> TYPE: DNA
<213> ORGANISM: Artificial Sequence
<220> FEATURE:
<223> OTHER INFORMATION: PSMB4 forward primer

<400> SEQUENCE: 32
ttcactggcc actggttatg                                                  20

<210> SEQ ID NO 33
<211> LENGTH: 20
<212> TYPE: DNA
<213> ORGANISM: Artificial Sequence
<220> FEATURE:
<223> OTHER INFORMATION: PSMB4 reverse primer mouse
```

<400> SEQUENCE: 33
cgaacgggca tctctgtagt                                               20

<210> SEQ ID NO 34
<211> LENGTH: 20
<212> TYPE: DNA
<213> ORGANISM: Artificial Sequence
<220> FEATURE:
<223> OTHER INFORMATION: PSMB7 forward primer mouse

<400> SEQUENCE: 34
ctgtcttgga agcggatttc                                               20

<210> SEQ ID NO 35
<211> LENGTH: 20
<212> TYPE: DNA
<213> ORGANISM: Artificial Sequence
<220> FEATURE:
<223> OTHER INFORMATION: PSMB7 reverse primer mouse

<400> SEQUENCE: 35
gcaacaacca tcccttcagt                                               20

<210> SEQ ID NO 36
<211> LENGTH: 20
<212> TYPE: DNA
<213> ORGANISM: Artificial Sequence
<220> FEATURE:
<223> OTHER INFORMATION: PSMC1 forward primer mouse

<400> SEQUENCE: 36 aaggggtca ttctctacgg                                                20

<210> SEQ ID NO 37
<211> LENGTH: 20
<212> TYPE: DNA
<213> ORGANISM: Artificial Sequence
<220> FEATURE:
<223> OTHER INFORMATION: PSMC1 reverse primer mouse

<400> SEQUENCE: 37
aagctctgag ccaaccactc                                               20

<210> SEQ ID NO 38
<211> LENGTH: 20
<212> TYPE: DNA
<213> ORGANISM: Artificial Sequence
<220> FEATURE:
<223> OTHER INFORMATION: PSMC4 forward primer mouse

<400> SEQUENCE: 38
tggtcatcgg tcagttcttg                                               20

<210> SEQ ID NO 39
<211> LENGTH: 20
<212> TYPE: DNA
<213> ORGANISM: Artificial Sequence
<220> FEATURE:
<223> OTHER INFORMATION: PSMC4 reverse primer mouse

<400> SEQUENCE: 39
cggtcgatgg tactcaggat                                               20

<210> SEQ ID NO 40

```
<211> LENGTH: 20
<212> TYPE: DNA
<213> ORGANISM: Artificial Sequence
<220> FEATURE:
<223> OTHER INFORMATION: PSMD1 forward primer mouse

<400> SEQUENCE: 40 gggcttttg aggagtctct                                              20

<210> SEQ ID NO 41
<211> LENGTH: 20
<212> TYPE: DNA
<213> ORGANISM: Artificial Sequence
<220> FEATURE:
<223> OTHER INFORMATION: PSMD1 reverse primer mouse

<400> SEQUENCE: 41
gcaaatctgc attttccaca                                              20

<210> SEQ ID NO 42
<211> LENGTH: 20
<212> TYPE: DNA
<213> ORGANISM: Artificial Sequence
<220> FEATURE:
<223> OTHER INFORMATION: PSMD12 forward primer

<400> SEQUENCE: 42
tcacagacct gccagtcaag                                              20

<210> SEQ ID NO 43
<211> LENGTH: 20
<212> TYPE: DNA
<213> ORGANISM: Artificial Sequence
<220> FEATURE:
<223> OTHER INFORMATION: PSMD 12 reverse primer

<400> SEQUENCE: 43
aggttttagt cagccgagca                                              20

<210> SEQ ID NO 44
<211> LENGTH: 20
<212> TYPE: DNA
<213> ORGANISM: Artificial Sequence
<220> FEATURE:
<223> OTHER INFORMATION: PSMD12 forward primer mouse

<400> SEQUENCE: 44
aactttggca ttgtggaagg                                              20

<210> SEQ ID NO 45
<211> LENGTH: 20
<212> TYPE: DNA
<213> ORGANISM: Artificial Sequence
<220> FEATURE:
<223> OTHER INFORMATION: GAPDH reverse primer mouse

<400> SEQUENCE: 45
ggatgcaggg atgatgttct                                              20
```